United States Patent [19]
Cook et al.

[11] Patent Number: 6,001,841
[45] Date of Patent: Dec. 14, 1999

[54] CYCLOBUTYL OLIGONUCLEOTIDE SURROGATES

[75] Inventors: Phillip Dan Cook, Carlsbad, Calif.; Gerhard Baschang, Bettingen, Switzerland

[73] Assignee: Isis Pharmaceuticals, Inc., Carlsbad, Calif.

[21] Appl. No.: 08/287,691

[22] Filed: Aug. 9, 1994

Related U.S. Application Data

[63] Continuation of application No. 07/808,201, Dec. 13, 1991, Pat. No. 5,359,044.

[51] Int. Cl.$^6$ .......................... A01N 67/00; A01N 43/54; A01N 43/90
[52] U.S. Cl. .......................... 514/261; 514/81; 514/269; 514/274
[58] Field of Search .............................. 514/81, 261, 269, 514/274

[56] References Cited

U.S. PATENT DOCUMENTS

| | | | |
|---|---|---|---|
| 4,918,075 | 4/1990 | Zahler et al. | 514/262 |
| 5,034,506 | 7/1991 | Summerton et al. | 528/391 |
| 5,087,617 | 2/1992 | Smith | 514/44 |
| 5,126,345 | 6/1992 | Slusarchyk et al. | 514/254 |
| 5,138,045 | 8/1992 | Cook et al. | 536/27 |
| 5,223,618 | 6/1993 | Cook et al. | 544/276 |
| 5,246,931 | 9/1993 | Norbeck et al. | 514/242 |
| 5,369,098 | 11/1994 | Slusarchyk | 514/81 |
| 5,378,825 | 1/1995 | Cook et al. | 536/25.34 |

FOREIGN PATENT DOCUMENTS

| | | |
|---|---|---|
| 2 336 059 A2 | 5/1990 | European Pat. Off. . |
| 86/05518 | 9/1986 | WIPO . |
| 91/10671 | 7/1991 | WIPO . |
| 91/14436 | 10/1991 | WIPO . |

OTHER PUBLICATIONS

Avram, M., "Untersuchungen in der Cyclobuanreihe, I" *Chem. Ber.*, 1957 90, 1424–1432.

Boumchita, H., "New Cyclobutyl Analogs of Adenosine and Guanosine. Part 1. Synthesis of the 9–[3,3–Bis(hydroxymethyl)cyclobutyl]purine Nucleoside Analogs" *J. Heterocyclic Chem.* 27:1815–1819 (1990).

Goodchild, J. "Conjugates of Oligonucleotides and Modified Oligonucleotides: A Review of Their Synthesis and Properties" Bioconjugate Chemistry, 1:165–187 (1990).

Gryaznov, S.M. and Sokolova, N.I., "A New Method for the Synthesis of Oligodeoxyribonucleotides Containing Internucleotide Phosphoramidate Bonds" Tetrahedron Letters, 1990 31, 3205–3208.

Hayashi, S., "Cyclobut–A and Cyclobut–G, Carbocyclic Oxetanocin Analogs That Inhibit the Replication of Human Immunodeficiency Virus in T Cells and monocytes and Macrophages In Vitro" Antimicrobial Agents and Chemotherapy, 34:287–294 (1990).

Henlin et al., "Synthesis of Octameric Phosphodiesters of [3,3–Bis(hydroxymethyl) cyclobutyl]adenine and –Thymine as Well as Their Hybridization Properties", *Angewandte* vol. 31, No. 4: 482–484 (1992).

Henlin et al., "Synthesis of 3–Adenyl–and 3–Thyminylcyclobutane–1, 1–dimethanols and Their Homo–octameric Phosphodiesters", *Helvetica Chimica Acta* vol. 75: 589–603 (1992).

Ito, H., "Solid Phase Synthesis of Polynucleotides. VI Further Studies on Polystyrene Copolymers for the Solid Support" *Nucleic Acids Research*, 1982, 10, 1755–1769.

Li, C and Zemlicka "Simple Models of Nucleic Acid Interactions. 2. Aminoacyl Derivatives of "Bridged" Nucleosides: Synthesis of 2'(3')–O–L–Phenylalanyl–and 2'(3')–O–1–Leucyl–1,2–di (adenosin–N$^6$–yl)ethane" *J.Organic Chem.* 1977 42, 706–711.

Maruyama, T. et al., "Synthesis and Antiviral Activities of Carbocyclic Oxetanocin Analogues" J. Chem. Pharm. Bull., 38 (1990) 2719–2725.

Matteucci, M. "Deoxyoligonucleotide Analgos Based on Formacetal Linkages" Tetrahedron Letters, 31: 2385–2388 (1990).

Mazur, A., "Isoteres of Natural Phosphates. 11. Synthesis of a phosphonic Acid Analgoue of an Oligonucleotide" Tetrahedron, 40:3949–3956 (1984).

Miller and Ts'o, "A New Approach to Chemotherapy Based on Molecular Biology and Nucleic Acid Chemistry: Matagen (Masking Tape for Gene Expression)" Anti Cancer Drug Design 2:117–128 ( ).

Musicki, B "Synthesis of Carbohydrates Sulfonates and Sulfonate Esters" *J. Organic Chem.*, 1990, 55, 4231–4233.

Norbeck, D.W., "Cyclobut–A and Cyclobut–G: Broad–Spectrum Antiviral Agents with Potential Utility for the Therapy of AIDS" J. Med. Chem., 33:1281–12185 (1990).

Nyilas, A. et al., "Synthesis of [3' (O) –5' (C)] Oxyacetamido Linked Nucleosides" *Tetrahedron* 1990 46, 2149–2164.

Ogilvie and Cormier, "Synthesis of a Thymidine Dinucleotide Analogue Containing an Internucleotide Silyl Linkage" *Tet. Letts.* 1985 26 4159–4162.

Pfitzner and Moffatt, "The synthesis of nucleoside–5' aldehydes", *J. Am. Chem. Soc.*, 1963 85, 3027.

Radhakrishnan, P.I. "3H–1,2–Benzodithiole–3–one 1,1–Dioxide as an Improved Sulfurizing Reagent in the Solid–Phase Synthesis of Oligodeoxyribonuleoside Phosporothioates" *J. Am. Chem. Soc.*, 1990 112, 1253–1254.

Rink, H., "A Large Fragment Approach to DNA Synthesis: Total Synthesis of a Gene for the Protease Inhibitor Eglin C from the Leech hirudo Medicinalis and its Expression in *E. Coli*", *Nucleic Acids Research* 1984 12, 6369–6387.

(List continued on next page.)

*Primary Examiner*—Russell Travers
*Attorney, Agent, or Firm*—Woodcock Washburn Kurtz Mackiewicz & Norris LLP

[57] ABSTRACT

Oligonucleotide surrogates comprising a plurality of cyclobutyl moieties covalently joined by linking moieties are prepared and used as antisense diagnostics, therapeutics and research reagents. Methods of synthesis and use of both the oligonucleotide surrogates and intermediates thereof are disclosed.

8 Claims, No Drawings

OTHER PUBLICATIONS

Safanda, J. and Sobotka, P., "3–Aminocyclobutane–1–Carboxylic Acid: Synthesis and Some Neurochemical Properties" *Collect. Czech. Chem. Commun.* 1982 47, 2440–2447.

Stirchak, E.P. and Summerton, J.E. "Uncharged Stereoregular Nucleic Acid Analogues. 1. Synthesis of a Cytosine–Containing Oligomer with Carbamate Internucleoside Linkages" *J. Organic Chem.*, 1987, 52, 4202–4206.

Uhlmann, E. and A. Peyman, "Antisense Oligonucleotides: A New Therapeutic Principle," *Chem. Rev.* 1990 90 543–584.

Veeneman, G.H., "Synthesis of Oligodeoxynucletodies Containing Thymidines Linked Via an Internucleosidic–(3'–5')–Methylene Bond" *Recl. Trav. Chim, Pays–Bas* 1990 109, 449–451.

CYCLOBUTYL OLIGONUCLEOTIDE SURROGATES

CROSS REFERENCE TO RELATED APPLICATIONS

This application is a continuation of Ser. No. 07/808,201, filed Dec. 13, 1991 now U.S. Pat. No. 5,359,049. The entire contents of the foregoing patent application are incorporated herein by reference.

FIELD OF THE INVENTION

This application is directed to oligonucleotide surrogate compounds and their intermediates and to their design, synthesis and use. More particularly this invention is directed to oligonucleotide surrogate compounds that include linked cyclobutyl rings having heterocyclic bases attached thereto. Such oligonucleotide surrogates are useful for therapeutics, diagnostics and as research reagents.

BACKGROUND OF THE INVENTION

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in an effort to moderate their disease causing or disease potentiating functions. Recently, however, attempts have been made to moderate the actual production of such proteins by interactions with messenger RNA (mRNA) or other intracellular RNA's that direct protein synthesis. It is the general object of such therapeutic approaches to interfere with or otherwise modulate gene expression leading to undesired protein formation.

Antisense methodology is the complementary hybridization of relatively short oligonucleotides to single-stranded RNA or single-stranded DNA such that the normal, essential functions of these intracellular nucleic acids are disrupted. Hybridization is the sequence specific hydrogen bonding via Watson-Crick base pairs of the heterocyclic bases of oligonucleotides to RNA or DNA. Such base pairs are said to be complementary to one another.

Naturally-occurring events that provide for the disruption of the nucleic acid function, as discussed by Cohen in *Oligonucleotides: Antisense Inhibitors of Gene Expression*, CRC Press, Inc., Boca Raton, Fla. (1989), are thought to be of two types. The first is hybridization arrest. This denotes the terminating event in which an oligonucleotide inhibitor binds to the target nucleic acid and thus prevents, by simple steric hindrance, the binding of essential proteins, most often ribosomes, to the nucleic acid. Methyl phosphonate oligonucleotides: Miller, P. S. and Ts'O, P. O. P. (1987) *Anti-Cancer Drug Design*, 2:117–128, and α-anomer oligonucleotides are the two most extensively studied antisense agents that are thought to disrupt nucleic acid function by hybridization arrest.

In determining the extent of hybridization arrest of an oligonucleotide, the relative ability of an oligonucleotide to bind to complementary nucleic acids may be compared by determining the melting temperature of a particular hybridization complex. The melting temperature ($T_m$), a characteristic physical property of double helixes, denotes the temperature in degrees centigrade at which 50% helical versus coil (unhybridized) forms are present. $T_m$ is measured by using the UV spectrum to determine the formation and breakdown (melting) of hybridization. Base stacking which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$.

The second type of terminating event for antisense oligonucleotides involves the enzymatic cleavage of the targeted RNA by intracellular RNase H. A 2'-deoxyribofuranosyl oligonucleotide hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides as antisense agents for diagnostics, research reagents and potential therapeutic purposes. This research has included the synthesis of oligonucleotides having various modifications. Such modification have primarily been modifications of the phosphate links that connect the individual nucleosides of the oligonucleotide. Various phosphorothioates, phosphotriesters, phosphoramidates and alkyl phosphonates have been reported. Further research has been directed to replacement of the inter-nucleoside phosphates with other moieties such as carbamates, sulfonates, siloxanes and the formacetal group. Other modifications have been effected wherein conjugate groups are attached to the nucleosides of the oligonucleotide via linking groups. Such conjugates include fluorescent dyes, intercalating agents, proteins, cross-linking agents, chain-cleaving agents and other groups including biotin and cholesterol. An extensive review discussing all of these modifications is that of Goodchild, J. (1990) *Bioconjugate Chemistry*, 1:165.

Since the heterocyclic bases of the nucleosides of an antisense oligonucleotide are necessary for the proper Watson/Crick binding of the antisense oligonucleotide to the target RNA or DNA, with the exception of cross-linking agents, little has been reported as to modification on the heterocyclic bases.

"Alpha" nucleosides have been used to form oligonucleotides having "alpha" sugars incorporated therein. In a like manner 2'-O-methylribonucleotides also have been used as precursor building blocks for oligonucleotides. U.S. Pat. No. 5,034,506 and PCT Patent Application PCT/US86/00544 suggest that the sugar portion of a nucleoside can be ring opened via oxidization and then ring closed by reactions with an amino or hydrazine group on an adjacent nucleoside. This links the nucleosides. Further, upon ring closure with the amino or hydrazine group, a new ring, a morpholine ring, is formed from the residue of the oxidized pentofuranose sugar ring of the nucleoside. PCT/US86/00544 also suggests that a linear amino acid based polymer might be used in place of a sugar-phosphate backbone to link heterocyclic bases together in an oligonucleotide-like linkage. Aside from these modifications, modification of the sugar moieties of the nucleosides of oligonucleotides is also little known.

In a further approach to modification of oligonucleotides both the sugar moieties and the phosphate linkers have been removed and replaced by a polymeric backbone. Utilizing this approach, heterocyclic bases have been tethered to various polymers including poly(N-vinyl), poly (methacryloxyethyl), poly(methacrylamide), poly (ethyleneimine) and poly(lysine). These types of compounds generally suffer from inappropriate spatial orientation of the heterocyclic bases for proper hybridization with a target RNA or DNA. A review of such polymeric compounds and the before noted "alpha" sugar containing oligonucleotides and 2'-O-methylribonucleotides is found in Uhlmann, E. and Peyman, A., (1990) *Chemical Reviews*, 90:543.

Recently oxetanocin and certain of its carbocyclic analogs have been studied as antiviral chemotherapeutic agents. These compounds incorporate an oxetane or a cyclobutane ring in place of the sugar moiety of a nucleoside. Cyclobut-A, i.e. (±)-9-[(1β, 2α, 3β)-2,3-bis-(hydroxymethyl)-1-cyclobutyl]adenine, and cyclobut-G, i.e. (±)-9-[(1β,2α,3β)-2,3-bis(hydroxymethyl)-1-cyclobutyl]guanine, were reported by Norbeck, D. W., Kern, E. Hayashi, S., Rosenbrook, W., Sham, H., Herrin, T., Plattner, J. J., Erickson, J., Clement, J., Swanson, R., Shipkowitz, N., Hardy, D., Marsh, K., Arnett, G., Shannon, W., Broder, S. and Mitsuya, H. (1990) *J. Med. Chem.*, 33:1281. Further antiviral activity of these compounds was reported by Hayashi, S., Norbeck, D. W., Rosenbrook, W., Fine, R. L., Matsukura, M., Plattner, J. J., Broder, S. and Mitsuya, H. (1990) *Antimicrobial Agents and Chemotherapy*, 34:287. As reported in Hayashi et. al., both cyclobut-A and cyclobut-G exist as racemic mixtures of diastereomers. Also as reported by Hayashi et. al., the thymine, uracil and hypoxanthine analogs of cyclobut-A and cyclobut-G did not exhibit antiviral activity.

In an attempt to eliminate any effects that the racemic, diastereomeric 2,3-bis(hydroxymethyl)-1-cyclobutyl portion of cyclobut-A and cyclobut-G might have towards phosphorylation by kinases, non-diastereomeric 3,3-bis(hydroxymethyl)-1-cyclobutyl analogs of cyclobut-A and cyclobut-G were synthesized and reported by Boumchita, H., Legraverenc, M., Huel, C. and Bisagni, E. (1990) *J. Heterocyclic Chem.* 27:1815. However, contrary to the activity of cyclobut-A and cyclobut-G, the 3,3-bis(hydroxymethyl)-1-cyclobutyl analogs of adenine and guanine, i.e. 9-[3,3-bis(hydroxymethyl)cyclobut-1-yl]jadenine and 9-[3,3-bis(hydroxymethyl)cyclobut-1-yl]guanine, respectively, were found to be devoid of antiviral activity.

OBJECTS OF THE INVENTION

It is one object of this invention to provide oligonucleotide surrogate compounds that incorporate cyclobutyl moieties.

It is a further object to provide cyclobutyl-based oligonucleotide surrogate compounds that have antisense hybridizability against DNA and RNA sequences.

It is another object of this invention to provide cyclobutyl-based oligonucleotide surrogate compounds for use in antisense diagnostics and therapeutics.

A still further object is to provide research and diagnostic methods and materials for assaying bodily states in animals, especially diseased states.

Another object is to provide therapeutic and research methods and materials for the treatment of diseases through modulation of the activity of DNA and RNA.

It is yet another object to provide methods for synthesizing sequence-specific cyclobutyl-based oligonucleotide surrogate compounds.

These and other objects will become apparent to the art skilled from a review of this specification and the claims appended hereto.

BRIEF DESCRIPTION OF THE INVENTION

In accordance with this invention there are provided oligonucleotide surrogates that are formed from a plurality of cyclobutyl moieties that are covalently joined by linking moieties; each of the cyclobutyl moieties has one of a purine or a pyrimidine heterocyclic base attached to it.

In preferred oligonucleotide surrogates of the invention the purine or pyrimidine heterocyclic base is a naturally-occurring or synthetic purin-9-yl, pyrimidin-1-yl or pyrimidin-3-yl heterocyclic base. Preferably, the purine or pyrimidine heterocyclic base is adenine, guanine, cytosine, thymidine, uracil, 5-methylcytosine, hypoxanthine or 2-aminoadenine.

In preferred oligonucleotide surrogates the heterocyclic base is attached to each respective cyclobutyl moiety at the carbon-1 (C-1) position of said cyclobutyl moiety and the linking moieties connect to each respective cyclobutyl moiety at the carbon-3 (C-3) position thereof. In these preferred embodiments, a substituent group can be located on one of the carbon-2 (C-2) or the carbon-4 (C-4) positions of at least one of the cyclobutyl moieties. Preferred substituents include halogen, $C_1$–$C_{10}$ alkoxy, allyloxy, $C_1$–$C_{10}$ alkyl or $C_1$–$C_{10}$ alkylamine groups. Preferably, the substituent group is positioned trans to the heterocyclic base.

In preferred oligonucleotide surrogates of the invention, the linking moieties are 4 or 5 atoms chains that connect adjacent cyclobutyl moieties. When the linking moieties are 5 atoms chains, each of the linking moieties preferably is of the structure $L_1$—$L_2$—$L_3$, where $L_1$ and $L_3$ are $CH_2$; and $L_2$ is phosphodiester, phosphorothioate, phosphoramidate, phosphotriester, $C_1$–$C_6$ alkyl phosphonate, phosphorodithioate, phosphonate, carbamate, sulfonate, $C_1$–$C_6$-dialkylsilyl or formacetal. Preferably, each of the linking moieties is of the structure $L_1$—$L_2$—$L_3$, where L, and $L_3$ are $CH_2$ and $L_2$ is phosphodiester or phosphorothioate.

When the linking moieties are 4 atom chains, each of the linking moieties preferably is of the structure:

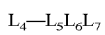

where:
(a) $L_4$ and $L_7$ are $CH_2$; and $L_5$ and $L_6$, independently, are $CR_1R_2$, $C=CR_1R_2$, $C=NR_3$, $C=O$, $C=S$, O, S, SO, $SO_2$, $NR_3$ or $SiR_4R_5$; or (b) $L_4$ and $L_7$ are $CH_2$; and $L_5$ and $L_6$, together, are $CR_1=CR_2$, $C\equiv C$, part of a $C_6$ aromatic ring, part of a $C_3$-$C_6$ carbocyclic ring or part of a 3, 4, 5 or 6 membered heterocyclic ring; or (c) $L_4$—$L_5$—$L_6$—$L_7$, together, are CH=N—NH—$CH_2$ or $CH_2$—O—N=CH;

wherein:
$R_1$ and $R_2$, independently, are H, OH, SH, $NH_2$, $C_1$–$C_{10}$ alkyl, $C_1$–$C_{10}$ substituted alkyl, $C_1$–$C_{10}$ alkenyl, $C_7$–$C_{10}$ aralkyl, $C_1$–$C_6$ alkoxy, $C_1$–$C_6$ thioalkoxy, $C_1$–$C_6$ alkylamino, $C_7$–$C_{10}$ aralkylamino, $C_1$–$C_{10}$ substituted alkylamino, heterocycloalkyl, heterocycloalkylamino, aminoalkylamino, polyalkylamino, halo, formyl, keto, benzoxy, carboxamido, thiocarboxamido, ester, thioester, carboxamidino, carbamyl, ureido, guanidino, an RNA cleaving group, a group for improving the pharmacokinetic properties of an oligonucleotide, or a group for improving the pharmacodynamic properties of an oligonucleotide;

$R_3$ is H, OH, $NH_2$, $C_1$–$C_6$ alkyl, substituted lower alkyl, alkoxy, lower alkenyl, aralkyl, alkylamino, aralkylamino, substituted alkylamino, heterocycloalkyl, heterocycloalkylamino, aminoalkylamino, polyalkylamino, a RNA cleaving group, a group for improving the pharmacokinetic properties of an oligonucleotide and a group for improving the pharmacodynamic properties of an oligonucleotide; and $R_4$ and $R_5$, independently, are $C_1$–$C_6$ alkyl or alkoxy. Particularly preferred 4 atom linking moieties are CH=N—NH—CH$_2$, CH$_2$—NH—NH—CH$_2$, CH$_2$—O—NH—CH$_2$ or CH$_2$—O—N=CH.

Further in accordance with this invention there is provided a method for modulating the production or activity of a protein in an organism, comprising contacting the organism with an oligonucleotide surrogate formulated in accordance with the forgoing considerations. Such an oligonucleotide surrogate is specifically hybridizable with at least a portion of a nucleic acid sequence, i.e. an RNA or DNA, coding for the protein. At least a portion of the oligonucleotide surrogate is formed from a plurality of linked cyclobutyl moieties, each moiety having an attached purine or pyrimidine heterocyclic base.

Additionally in accordance with this invention there is provided a method of treating an organism having a disease characterized by the undesired production of a protein. This method includes contacting the organism with an oligonucleotide surrogate also formulated in accordance with foregoing considerations. Such an oligonucleotide surrogate is specifically hybridizable with at least a portion of a nucleic acid sequence, i.e. an RNA or DNA sequence, coding for the protein whose production or activity is to be modulated. At least a portion of the oligonucleotide surrogate is formed from a plurality of linked cyclobutyl moieties, wherein each moiety having an attached purine or pyrimidine heterocyclic base.

Further in accordance with this invention there is provided a pharmaceutical composition containing as its active ingredient an effective amount of an oligonucleotide surrogate formed from a plurality of linked cyclobutyl moieties, each moiety having an attached purine or pyrimidine heterocyclic base; and a pharmaceutically acceptable diluent or carrier.

Even further in accordance with this invention there is provided a method of in vitro assaying a sequence specific nucleic acid, i.e. an RNA or DNA, comprising contacting an in vitro composition which includes the nucleic acid with an oligonucleotide surrogate that is specifically hybridizable with at least a portion of the nucleic acid. The oligonucleotide surrogate preferably is formulated in accordance with the foregoing considerations. Thus, at least a portion of the oligonucleotide surrogate compound is formed from a plurality of linked cyclobutyl moieties, each moiety having an attached purine or pyrimidine heterocyclic base.

Even further in accordance with this invention there is provided a process for the preparation of a compound formed from a plurality of linked cyclobutyl moieties wherein each moiety has an attached purine or pyrimidine heterocyclic base. The process comprises the steps of: functionalizing the cyclobutyl moieties with a leaving group; displacing the leaving group on each of the cyclobutyl moieties with an independently selected purine or pyrimidine heterocyclic base; functionalizing each of the base-containing cyclobutyl moieties with a protecting group; further functionalizing the protected moieties with an activated linking group; and stepwise deprotecting and linking the heterocyclic-base-containing cyclobutyl moieties. Such processes can be augmented to include stepwise deprotection and linkage of the base-containing cyclobutyl moieties on a polymeric support. In a preferred embodiment of this process, the base-containing cyclobutyl moieties are stepwise deprotected and linked together by: (a) deprotecting a first of the protected moieties; (b) linking a further of the protected moieties bearing an activated linking group with the deprotected moiety to form a linked structure; and (c) deprotecting the linked structure. Deprotecting and linking steps (b) and (c) preferably are repeated a plurality of times.

Even further in accordance with this invention there is provided an antiviral composition containing as its active ingredient an effect amount of a compound of structure (A):

STRUCTURE (A)

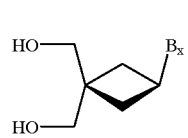

wherein $B_x$ is purin-9-yl, pyrimidin-1-yl or pyrimidin-3-yl; and a pharmaceutically acceptable diluent or carrier.

Additionally in accordance with this invention there is provided a method of treating viral diseases in mammals comprising administering to the mammal a therapeutic amount of a composition containing as its active ingredient a compound of the structure (A). In preferred embodiments, the viral disease is a herpes viral disease.

DETAILED DESCRIPTION OF THE INVENTION

In the context of this invention, the term "nucleoside" refers to a molecular species made up of a heterocyclic base and a sugar. In naturally-occurring nucleosides, the heterocyclic base typically is guanine, adenine, cytosine, thymine, or uracil. Other natural bases are known, as are a plenitude of synthetic or "modified" bases. In naturally-occurring nucleosides, the sugar is normally deoxyribose (DNA type nucleosides) or ribose (RNA type nucleosides). Synthetic sugars also are known, including arabino, xylo or lyxo pentofuranosyl sugars and hexose sugars. Historically, the term nucleoside has been used to refer to both naturally-occurring and synthetic species formed from naturally-occurring or synthetic heterocyclic base and sugar subunits.

The term "nucleotide" refers to a nucleoside having a phosphate group esterified to one of its 2', 3' or 5' sugar hydroxyl groups. The phosphate group normally is a monophosphate, a diphosphate or triphosphate. The term "oligonucleotide" normally refers to a plurality of joined monophosphate nucleotide units. These units are formed from naturally-occurring bases and pentofuranosyl sugars joined by native phosphodiester bonds. A homo-oligonucleotide is formed from nucleotide units having a common heterocyclic base.

The term "oligonucleotide analog" has been used to refer to molecular species which are structurally similar to oligonucleotides but which have non-naturally-occurring portions. This term has been used to identify oligonucleotide-like molecules that have altered sugar moieties, altered base moieties, or altered inter-sugar linkages. Thus, the term oligonucleotide analog denotes structures having altered inter-sugar linkages such as phosphorothioate, methyl phosphonate, phosphotriester or phosphoramidate internucleoside linkages in place of native phosphodiester internucleoside linkages; purine and pyrimidine heterocyclic bases other than guanine, adenine, cytosine, thymine or uracil; carbocyclic or acyclic sugars; sugars having other than the β pentofuranosyl configuration; or sugars having substituent groups at their 2' position or at one or more of the sugar hydrogen atoms.

Certain oligonucleotide analogs having non-phosphodiester bonds, i.e. an altered inter-sugar linkage, can be referred to as "oligonucleosides." The term oligonucleoside thus refers to a plurality of joined nucleoside units joined by linking groups other than native phosphodiester linking groups. Additionally, the term "oligomers" can be used to encompass oligonucleotides and oligonucleotide analogs. Generally, the inter-sugar linkages of oligonucleotides and oligonucleotide analogs are from the 3' carbon of one nucleoside to the 5' carbon of a second nucleoside; however, the terms oligomer and oligonucleotide analog also have been used in reference to 2'–5' linked oligonucleotides.

Antisense therapy is the use of oligonucleotides or oligonucleotide analogs to bind with complementary strands of RNA or DNA. After binding, the oligonucleotide and the RNA or DNA strand are "duplexed" together in a manner analogous to native, double-stranded DNA. The oligonucleotide strand and the RNA or DNA strand can be considered complementary strands wherein the individual strands are positioned with respect to one another to allow Watson/Crick type hybridization of the heterocyclic bases of one strand to the heterocyclic bases of the opposing strand.

Antisense therapeutics can be practiced in a plethora of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to antisense therapeutics and/or prophylactics. Seemingly diverse organisms such as bacteria, yeast, protozoa, algae, and all plant and all higher animal forms, including warm-blooded animals, can be treated by antisense therapy. Further, since each of the cells of multicellular eukaryotes includes both DNA-RNA transcription and RNA-protein translation as an integral part of their cellular activity, antisense therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations and organelles can also be included within the definition of organisms that are capable of being treated with antisense therapeutics or diagnostics. As used herein, therapeutics is meant to include both the eradication of a disease state, killing of an organism, e.g. bacterial, protozoan or other infection, or control of erratic or harmful cellular growth or expression.

Antisense therapy utilizing "oligonucleotide analogs" is exemplified in the disclosures of the following United States and PCT Patent Applications: Ser. No. 463,358, filed Jan. 11, 1990, entitled Compositions And Methods For Detecting And Modulating RNA Activity; Ser. No. 566,836, filed Aug. 13, 1990, entitled Novel Nucleoside Analogs; Ser. No. 566,977, filed Aug. 13, 1990, entitled Sugar Modified oligonucleotides That Detect And Modulate Gene Expression; Ser. No. 558,663, filed Jul. 27, 1990, entitled Novel Polyamine Conjugated Oligonucleotides;, Ser. No. 558,806, filed Jul. 27, 1991, entitled Nuclease Resistant Pyrimidine Modified Oligonucleotides That Detect And Modulate Gene Expression; Ser. No. 703,619, filed May 21, 1991, entitled Backbone Modified Oligonucleotide Analogs; Ser. No. PCT/US91/00243, filed Jan. 11, 1991, entitled Compositions and Methods For Detecting And Modulating RNA Activity; and Ser. No. PCT/US91/01822, filed Mar. 19, 1991, entitled Reagents and Methods For Modulating Gene Expression Through RNA Mimicry. The foregoing applications are assigned to the assignee of this invention. The disclosure of each is incorporated herein by reference.

This invention is directed to certain molecular species which are related to oligonucleotides but which do not include a sugar moiety. In this invention, cyclobutane rings, i.e. cyclobutyl moieties, having heterocyclic bases attached thereto are connected by linking moieties into oligonucleotide-like structures. Such structures, while chemically different from oligonucleotides (or oligonucleotide analogs), are functionally similar. Such molecular species are therefore oligonucleotide surrogates. As oligonucleotide surrogates they serve as substitutes for oligonucleotides. We have found that they are capable of hydrogen bonding to complementary strands of DNA or RNA in the same manner as are oligonucleotides.

As will be recognized, a cyclobutane ring system may be considered as fixed when compared to a pentofuranose ring system. Thus, while a pentofuranose ring system allows for rotation about intra-ring chemical bonds, a cyclobutane ring system does not. Consequently, the pentofuranosyl ring system can "pucker"; a cyclobutane ring can only adopt two conformations. However, like a pentofuranosyl ring, a cyclobutane ring system has a sufficient number of functional positions within the ring to allow for placement of a number of substituent functional groups.

The nomenclature of nucleoside chemistry utilizes un-primed numbers to identify the functional positions on the heterocyclic base portion of the nucleoside and primed numbers to identify the functional positions on the sugar portion of the nucleoside. Further, the β isomer of a ribofuranosyl ring is syn about the anomeric C-1 position with respect to the C-5 carbon, while the α isomer is trans with respect to the C-5 carbon. IUPAC recommended nomenclature for the functional positions of cyclobutane differ from such standard nucleoside nomenclature. Utilizing IUPAC nomenclature, the substitution of position C-1 in the cyclobutane ring is always α.

For the purposes of this invention, positional identification of the cyclobutane ring is made by reference to structure (B):

STRUCTURE (B)

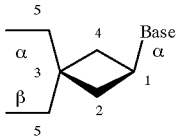

In the illustrative example below and the claims appended hereto, positional nomenclature is determined in a manner consistent with structure (B).

The oligonucleotide surrogates of the invention are formed by linking together a plurality of cyclobutyl moieties via linking moieties. Each of the cyclobutyl moieties includes a covalently-bound purine or pyrimidine heterocyclic base. Each of the linking moieties covalently bind two adjacent cyclobutyl moieties. Linked together in this manner, the cyclobutyl moieties present their heterocyclic bases in spatial positions for hybridization with DNA or RNA strands.

According to the present invention, cyclobutyl-based oligonucleotide surrogates include a plurality of subunits. Each subunit includes a cyclobutane ring, a heterocyclic base, and a linking moiety for joining adjacent subunits. The oligonucleotide surrogates of the invention preferably comprise from about 3 to about 100 subunits. Preferably, oligonucleotide surrogates comprise greater than about 6 subunits, preferably from about 8 to about 60 subunits, even more preferably from about 10 to about 30 subunits.

The heterocyclic base of each of the subunits can be a natural heterocyclic base or a synthetic heterocyclic base. In preferred embodiments the heterocyclic base is selected as a naturally-occurring or synthetic purin-9-yl, pyrimidin-1-yl or pyrimidin-3-yl heterocyclic base. Heterocyclic bases include but are not limited to adenine, guanine, cytosine, thymidine, uracil, 5-methylcytosine, hypoxanthine or 2-aminoadenine. Other such heterocyclic bases include 2-aminopurine, 2,6-diaminopurine, 6-mercaptopurine, 2,6-dimercaptopurine, 3-deazapurine, 6-amino-3-deazapurine, 6-amino-3-deaza-2-oxypurine, 2-amino-6-mercaptopurine, 5-methylcytosine, 4-amino-2-mercaptopyrimidine, 2,4-dimercaptopyrimidine, 5-fluorocytosine. Other suitable heterocyclic bases include those identified in patent application Ser. No. 558,806, filed Jul. 27, 1990, entitled Nuclease Resistant Pyrimidine Modified Oligonucleotides That Detect and Modulate Gene Expression and in PCT Patent Application US6/00544. The portions of these patent applications that set forth such heterocyclic bases are incorporated herein by reference.

In accordance with the invention, linking moieties are selected to covalently link individual heterocyclic-base-containing cyclobutyl moieties together in an orientation wherein the heterocyclic bases are positioned in space in a conformation which allows hybridization with a complementary strand of DNA or RNA.

In preferred embodiments of the invention the linking moieties are selected as 4 or 5 atoms chains. Such 4 and 5 atoms chains include the phosphodiester linkages of native DNA and RNA as well as the related synthetic phosphorothioate, phosphoramidate, alkyl phosphonate, phosphorodithioate and phosphotriester linkages of "oligonucleotide analogs." Other linking moieties include phosphate, carbamate, sulfonate, $C_1$-$C_6$-dialkylsilyl or formacetal linkages. Further linkages include an —O—$CH_2$—$CH_2$—O— linkage and the novel linkages disclosed in U.S. patent applications Ser. No. 566,836 and Ser. No. 703,619, identified above.

A preferred group of 5 atom linking moieties of the invention include linking moieties of the structure $L_1$—$L_2$—$L_3$ where $L_1$ and $L_3$ are $CH_2$; and $L_2$ is phosphodiester, phosphorothioate, phosphoramidate, phosphotriester, $C_1C_6$ alkyl phosphonate, phosphorodithioate, phosphonate, carbamate, sulfonate, $C_1$-$C_6$-dialkylsilyl or formacetal. A particularly preferred group of such 5 atom linker is of the structure $L_1$—$L_2$—$L_3$ where $L_1$ and $L_3$ are $CH_2$; and $L_2$ is phosphodiester or phosphorothioate.

A preferred group of 4 atoms linking moieties of the invention include linking moieties of the structure $L_4$—$L_5$—$L_6$—$L_7$ where:

$L_4$ and $L_7$ are $CH_2$; and $L_5$ and $L_6$, independently, are $CR_1R_2$, $C$=$CR_1R_2$, $C$=$NR_3$, $C$=$O$, $C$=$S$, $O$, $S$, $SO$, $SO_2$, $NR_3$ or $SiR_4R_5$; or $L_5$ and $L_6$, together, are $CR_1$=$CR_2$, $C$≡$C$, part of a $C_6$ aromatic ring, part of a $C_3$-$C_6$ carbocyclic ring or part of a 3, 4, 5 or 6 membered heterocyclic ring; or $L_4$-$L_5$—$L_6$—$L_7$, together, are CH=N—NH—$CH_2$ or $CH_2$—O—N=CH;

wherein:

$R_1$ and $R_2$, independently, are H, OH, SH, $NH_2$, $C_1$-$C_{10}$ alkyl, $C_1$-$C_{10}$ substituted alkyl, $C_1$-$C_{10}$ alkenyl, $C_7$-$C_{10}$ aralkyl, $C_1$-$C_6$ alkoxy, $C_1$-$C_6$ thioalkoxy, $C_1$-$C_6$ alkylamino, $C_7$-$C_{10}$ aralkylamino, $C_1$-$C_{10}$ substituted alkylamino, heterocycloalkyl, heterocycloalkylamino, aminoalkylamino, polyalkylamino, halo, formyl, keto, benzoxy, carboxamido, thiocarboxamido, ester, thioester, carboxamidino, carbamyl, ureido, guanidino, an RNA cleaving group, a group for improving the pharmacokinetic properties of an oligonucleotide, or a group for improving the pharmacodynamic properties of an oligonucleotide;

$R_3$ is H, OH, $NH_2$, $C_1$-$C_6$ alkyl, substituted lower alkyl, alkoxy, lower alkenyl, aralkyl, alkylamino, aralkylamino, substituted alkylamino, heterocycloalkyl, heterocycloalkylamino, aminoalkylamino, polyalkylamino, a RNA cleaving group, a group for improving the pharmacokinetic properties of an oligonucleotide and a group for improving the pharmacodynamic properties of an oligonucleotide; and $R_4$ and $R_5$, independently, are $C_1$-$C_6$ alkyl or alkoxy.

Groups that enhance pharmacodynamic properties improve uptake of the oligonucleotide surrogates, enhance the resistance of the oligonucleotide surrogates to degradation, and/or strengthen sequence-specific hybridization with RNA. Groups that enhance pharmacokinetic properties improve the uptake, distribution, metabolism or excretion of the oligonucleotide surrogates. A particularly preferred group of 4 atom linking moieties includes CH=N—NH—$CH_2$, $CH_2$—NH—NH—$CH_2$, $CH_2$—O—NH—$CH_2$ and $CH_2$—O—N=CH.

In addition to heterocyclic bases and linking moieties, the cyclobutyl moieties of the invention can further include other substituent groups. For oligonucleotide surrogates of the invention having their heterocyclic base at position C-1 and the linking moieties at position C-3, such substituent groups can be located on one or both of the C-2 or the C-4 position. Preferred substituent groups include halogen, $C_1$-$C_{10}$ alkoxy, allyloxy, $C_1$-$C_{10}$ alkyl or $C_1$-$C_{10}$ alkylamine. Preferably the substituent group is positioned trans to said heterocyclic base.

Certain preferred embodiments of the invention take advantage of the symmetry of 3,3-bis-hydroxymethyl-cyclobutane substituted at the C-1 position with a heterocyclic base, as in structure (C).

STRUCTURE (C)

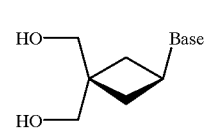

Compounds of this type can be synthesized by procedures which involve first preparing 1-heterocyclic, base-substituted derivatives of 1-benzyloxy-3,3-bis-hydroxymethyl-cyclobutane. These base-bearing compounds are then directly converted to their corresponding mono-O-substituted methoxytrityl derivatives. In one embodiment of the invention, the mono-O-substituted methoxytrityl derivatives are then converted to octameric phosphodiesters on an aminomethyl-polystyrene carrier utilizing the phosphotriester method of Van Boom, J. H., Van der Marel, G. A., Van Boeckel, C. A. A., Wille, G. and Hoyng, C. Chemical and Enzymatic Synthesis of Gene Fragments, A Laboratory Manual, edited by H. G. Gassen and Anne Lang, Verlag Chemie Weinheim/Deerfield Beach, Fla./Basel 1982.

Utilizing 1-benzyloxy-3,3-bis-hydroxymethyl-cyclobutane, "1-thyminyl-3,3-bis-hydroxymethyl-cyclobutane and 1-adenyl-3,3-bis-hydroxymethyl-cyclobutane" can be synthesized by direct introduction of the heterocyclic bases; uridyl-3,3-bis-hydroxymethylcyclobutane, 1-guanyl-3,3-bis-hydroxymethyl-cyclobutane and 1-cytidyl-3,3-bis-hydroxymethyl-cyclobutane are prepared by similar procedures, as are cyclobutanes substituted with other heterocyclic bases. To effect direct introduction of the heterocyclic base, the known 1-benzyloxy-3,3-bis-hydroxymethyl-cyclobutane is converted to the $O^5$, $O^{5'}$-isopropylidene-ether of 1-hydroxy-3,3-bis-hydroxymethyl-cyclobutane. Various sulfonate esters were examined for the introduction of the heterocyclic base. In the series mesylate, tosylate, brosylate and nosylate, the best properties with respect to stability and reaction conditions for substitution were observed with the p-bromobenzenesulfonate.

Introduction of adenine was accomplished in 90% yield in DMSO at 80° C. for 24 hours. Only the $N^9$-substituted product was detected by TLC. Substitution with 3 equivalents of thymine under the same conditions led to a mixture of 3 products: $N^1$-substituted (55%), disubstituted (34%) and traces of $N^3$-substituted product. Use of a four-fold excess of thymine did not suppress the formation of the disubstituted product. The desired heterocyclic-base-substituted compounds were purified by flash chromatography and were deprotected with hydrochloric acid in dioxane to yield corresponding 3,3-bis hydroxymethyl derivatives having an appropriate heterocyclic base at the C-1 position.

Reaction of the 1-heterocyclic-base-substituted 3,3-bis-hydroxymethyl-cyclobutanes with monomethoxytrityl chloride yielded the desired monomethoxytrityl derivatives. After separation of the isomers, these compounds can then directly be used to form oligonucleotide surrogates via phosphotriester oligonucleotide synthesis methods. Alternately, they may be converted to a corresponding phosphoramidate for use in the phosphoramidate oligonucleotide synthesis method.

Utilizing phosphotriester chemistry, reaction of 3,3-bis-hydroxymethyl-1-thiminyl-cyclobutane with 1.3 equivalents of monomethoxytrityl chloride in pyridine led to two monosubstituted products (35% and 42% yields, respectively) as well as the disubstituted derivative (9%) and unreacted starting material (6.5%). Addition of more methoxytrityl chloride did not diminish the amount of starting diol, but rather increased the amount of disubstituted product. The two mono-substituted isomers were each independently processed by the phosphotriester method to octameric phosphodiesters on a solid support with thymidine as a starting nucleoside.

Because of the asymmetry of the starting isomers, the resulting oligonucleotide surrogate compounds were of a pseudo-β- and a pseudo-α-configuration. The designation "pseudo-β" refers to an oligonucleotide surrogate of the invention formed from cyclobutane units having their heterocyclic base positioned cis to what would be the 5' position of a natural oligonucleotide; "pseudo-α" refers to oligonucleotide surrogates where the heterocyclic base would be trans to that same 5' position. The pseudo-α and pseudo-β configurations are shown in structures (D) and (E). A "normal" terminal thymidine nucleotide has been included in the structures at the "3'" terminal ends to better illustrate the configurations of the cyclobutane based oligonucleotide surrogates of the invention.

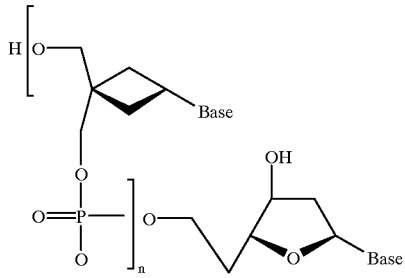

STRUCTURE (D) PSEUDO-α

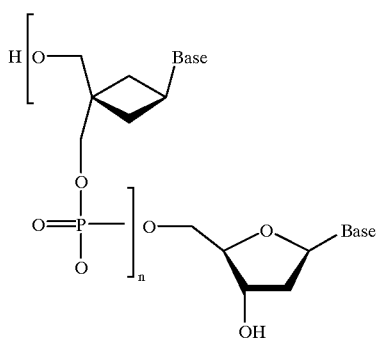

STRUCTURE (E) PSEUDO-β

In the adenine series (and in like manner in the guanine and cytosine series) the amino group of a 1-(heterocyclic base)-3,3-bis-hydroxymethyl-cyclobutane is first protected by benzoylation to provide the N,N-dibenzoate derivative in 95% a yield. This dibenzoate compound is then further converted to the desired isomers of $N^6$-benzoyl-$O^5$-methoxytrityl-3-hydroxymethyl-1-adenyl-cyclobutane in two different ways. Removal of the isopropylidene group prior to mono-debenzoylation with ammonia in THF proved to be more efficient compared to mono-debenzoylation prior to removal of the isopropylidene group. Following mono-debenzoylation and removal of the isopropylidene group, the resulting isomers of/the alcohols were again separately processed to octameric phosphodiesters on a solid support with 2-deoxy-adenosine as a starting nucleoside. This gave the desired pseudo-β- and pseudo-α-oligonucleotide surrogates. As a further aspect of this invention the cis and trans isomers of mono-hydroxymethyl substituted adenyl-cyclobutane were also prepared. A chromatographic separation of the cis and trans isomers of carboethoxy intermediates was utilized. The procedure was applied separately to both isomers of 1-benzyloxy-3-carbethoxy-cyclobutane. Reduction of the carbethoxy group with lithium aluminum hydride, protection with t-butyldiphenylsilyl chloride, hydrogenolytic removal of the benzyl group, introduction of the leaving group with p-bromo-benzenesulfonylchloride, and substitution with adenine in the presence of DBU in DMSO led to t-butyl-diphenylsilyl protected $N^9$-substituted adenine derivatives, together with the corresponding $N^7$-substituted derivatives. In both cases desired compounds were separated by chromatography. Final deprotection with hydrofluoric acid in urea gave the desired cis and trans 1-adenyl-3-hydroxymethyl-cyclobutanes.

For the introduction of $N^4$-isobutyryl-cytosine and 2-amino-6-methoxyethoxy-.purine (the corresponding guanine compound) the phenylsulfonyl leaving group proved to be the most efficient.

Syntheses of 1-adenyl-3,3-bis-hydroxymethyl-cyclobutane were recently reported by Maruyama, T., Sato, Y., Horii, T., Shiota, H., Nitta, K., Shirasaka, T., Mitsuya, H. and Honjo, J. (1990) *J. Chem. Pharm. Bull.*, 38:27–19 and Boumchita, H., Legraverend, M., Huel, C. and Bisagni, E. (1990) *J. Heterocyclic Chem.*, 27:1815. Both of these groups made use of a 1-amino derivative that was then elaborated to the end products by a stepwise synthesis of the heterocycle. This is to be contrasted with the teachings of this invention, wherein the heterocyclic bases are introduced directly by exploiting the preferential alkylation of these bases.

For the preparation of oligonucleotide surrogate compounds of the invention having phosphorothioate, phosphoramidate, phosphotriester, $C_1$–$C_6$ alkyl phosphonate and phosphorodithioate groups, the oligonucleotide synthetic methods based on phosphoramidate chemistry of the following, above-referenced United States and PCT Patent Applications: Ser. No. 566,836, Ser. No. 463,358, Ser. No. 558,806, Ser. No. 558,663, Ser. No. 566,977 and Ser. No. US91/00243. Briefly, protected 1-adenyl, guanyl or cytidyl or unprotected thyminyl and uridyl-3-monomethoxytrityl-3-hydroxymethyl-cyclobutane are phosphitylated and the resulting activated phosphate monomers are then joined to appropriate oligonucleotide surrogates. A phosphorothioate-type backbone is formed utilizing the Beaucage reagent, i.e. 3H-1,2-benzodithioate-3-one 1,1-dioxide, see Radhakrishnan, P. I., Egan, W., Regan, J. B. and Beaucage, S. L., (1990), *J. Am. Chem. Soc.*, 112:1253.

For the preparation of oligonucleotide surrogate compounds of the invention having 4 atom linking moieties, the synthetic methods of U.S. Pat. applications Ser. No. 566,836 and Ser. No. 703,619 are practiced. Specifically, the 3-hydroxymethyl group of a protected 1-adenyl, guanyl or cytosyl or unprotected thyminyl and uracyl-3-monoethoxytrityl-3-hydroxymethyl-cyclobutane is oxidized to the corresponding 3-aldehydic derivative by treatment with DMSO, benzene, DCC, pyridine and trifluoroacetic acid utilizing an oxidation procedure analogous to that of Pfitzer, K. E. and Moffat, J. G. (1963) *J. Am. Chem. Soc.*, 85:3027. The 3-aldehydic intermediate can be blocked for use as an aldehyde or it can be further converted to a hydrazino compound. Thus, the 3-aldehydic intermediate is either then treated with 1,2-dianilinoethylene to afford a 3-diphenylimidazolidino-protected 3-aldehydo compound or the 3-aldehydic intermediate is treated with hydrazine hydrate and sodium cyanoborohydride in acetonitrile to give the corresponding 3-hydrazino compound. These compounds are then used in further synthesis as per the teachings of above-noted patent application Ser. No. 703,619 to yield corresponding hydrazino and hydrazine-linked, heterocyclic-base-substituted cyclobutane dimers. Such dimers can be incorporated into the oligonucleotide surrogates or extended to form longer chain hydrazino or hydrazine-linked oligonucleotide surrogates. Thus, oligonucleotide surrogates of the invention having linking moieties of the structures CH=N—NH—$CH_2$ and $CH_2$—NH—NH—$CH_2$ are prepared in a facile manner.

Further protected 1-adenyl, guanyl or cytosyl or unprotected thyminyl and uracyl-3-monomethoxytrityl-3-hydroxymethyl-cyclobutane are converted to the corresponding 3-N-hydroxyphthalimide-3-monomethoxytrityl-3-hydroxymethyl-cyclobutanes by treatment of 3-monomethoxytrityl-3-hydroxymethyl-cyclobutane compounds with N-hydroxyphthalimide, triphenylphosphine, and diisopropylazodicarboxylate in dry DMF. The N-hydroxyphthalimido compound is then converted to a corresponding 3-amino intermediate compound by treatment with methylhydrazine in dry $CH_2Cl_2$ under anhydrous conditions, as per the teaching of above-referenced patent application Ser. No. 703,619.

Reaction of 3-amino cyclobutane compounds with 3-aldehydic cyclobutane compounds yield oxime-linked compounds. Such oximes can be reduced with sodium cyanoborohydride to form hydroxylamine linkages, if desired. Thus, oligonucleotide surrogates of the invention having linking moieties of the structures $CH_2$—O—NH—$CH_2$ and $CH_2$—O—N=CH are prepared in a facile manner.

Oligonucleotide surrogates of the invention having sulfonate linkages are prepared by reacting protected 1-adenyl, guanyl or cytosyl or unprotected thyminyl and uracyl-3-monoethoxytrityl-3-hydroxymethyl-cyclobutane as per the procedures of Musicki, B and Widlanski, T. S. (1990) *J. Organic Chem.*, 55:4231. Phosphoramidates linkages are formed as per the procedure of Gryaznov, S. M. and Sokolova, N. I. (1990) *Tetrahedron Letters*, 31:3205; formacetal linkages as per the procedure of Matteucci, M. (1990) *Tetrahedron Letters*, 31:2385; phosphonate linkages as per the procedure of Mazur, A., Troop, B. E. and Engel, R. (1984) *Tetrahedron*, 40:3949; carbamate linkages as per the procedure of Stirchak, E. P. and Summerton, J. E. (1987) *J. Organic Chem.*, 52:42–02; aminoacyl linkages as per the procedure of Li, C and Zemlicka (1977) *J. Organic Chem.*, 42:706 and Nyilas, A., Glemare, C. and Chattopadhyaya, J. (1990) *Tetrahedron*, 46:2149; methylene linkages as per the procedure of Veeneman, G. H., van der Marcel, G. A., van den Elst, H. and van Boom, J. H. (1990) *Recl. Trav. Chim. Pays-Bas*, 109:449; and silyl linkages as per the procedure of Ogilvie, K. K. and Cormier, J. F. (1985) *Tetrahedron Letters*, 26:4159.

The oligonucleotide surrogates of this invention can be used in diagnostics, therapeutics, and as research reagents and kits. For therapeutic use the oligonucleotide surrogates are administered to an animal suffering from a disease modulated by a protein. It is preferred to administer to patients suspected of suffering from such a disease an amount of the oligonucleotide surrogate that is effective to reduce the symptoms of that disease. One skilled in the art may determine optimum dosages and treatment schedules for such treatment regimens.

It is generally preferred to administer therapeutic oligonucleotide surrogates in accordance with this invention internally such as orally, intravenously, or intramuscularly. Other forms of administration, such as transdermally, topically, or intra-lesionally may also be useful. Inclusion in suppositories may also be useful. Use of the oligonucleotide surrogates of this invention in prophylaxis is also likely to be useful. Use of pharmacologically acceptable carriers is also preferred for some embodiments.

Additional objects, advantages, and novel features of this invention will become apparent to those skilled in the art upon examination of the following examples, which are not intended to be limiting.

Experimental

General—Flash chromatography: silica gel Merck 60, 230–400 mesh ASTM; Alumina B act I: ICN Biomedicals N° 02072; Hyflo: Fluka N° 56678; Molecular sieves: 0.4 and 0.3 nm, beads about 2 mm, Merck No 5704 and 5708; TLC plates: Merck silica gel 60 $f_{254}$ precoated, layer thickness: 0.25 mm; Solvents: Dichloromethane: stored over 0.4 nm molecular sieves; Dimethoxyethane (DME): passed over basic alumina before use; Dimethylsulfoxide (DMSO): distilled under vacuum and stored over 0.4 nm molecular sieves; Dioxane: passed over basic alumina before use;

Ethanol: stored over 0.3 nm molecular sieves; Pyridine: distilled and stored over 0.4 nm molecular sieves; Tetrahydrofuran (THF): distilled over potassium—naphthalene and stored over 0.4 nm molecular sieves; Toluene: distilled and stored over 0.4 nm molecular sieves; Triethylamine: distilled and stored over 0.4 nm molecular sieves; Solvents for chromatography: ratios given in v/v, distilled before use; Melting point: Büchi apparatus; I.R.: Perkin—Elmer model 881, film: 1 drop substance between 2 sodium chloride plates; NMR: 200 MHz: Varian GEM 200; 300 MHz: Varian GEM 300; 400 MHz: Bruker WM 400, solvent internal reference: $CDCl_3$: $^1H$: 7.265 PPM, $^{13}C$: 77.00 PPM; $CD_3OD$: $^1H$: 3.34 PPM, $^{13}C$: 49.00 PPM; DMSO: $^1H$: 2.50 PPM, $^{13}C$: 39.70 PPM; abbreviations: s, singlet; d, doublet; t, triplet; q, quadruplet; quint, quintuplet; Carbon NMR: completely decoupled and APT spectra were usually recorded, off-resonance decoupled spectra were recorded only if necessary; U. V.: Perkin—Elmer Lambda 9 UV/VIS/NIR spectrometer; M. S.: 2 AB, HF apparatus, FAB technique, thioglycerol as solvent: numbering on aromatic rings: r, reference; o, ortho; m, meta; p, para; on heterocyclics: adenine: ad+number; guanine: gu+number; thymine: thy+number; uracil: ur+number; cytosine: cy+number.

EXAMPLE 1

1-Benzyloxy-3,3-bis-carbethoxy-cyclobutane 1

Compound 1 was prepared according to the literature procedures of Avram, M., Nenitzescu, C. D. and Maxim, C. D. (1957) *Chem. Ber.*, 90:1424 and Safanda, J. and Sobotka, P. (1982) Collect. *Czech. Chem. Commun.* 47:2440 with minor improvements. Malonic acid diethyl ester (258.6 ml, 1.703 moles) was added neat over a two hours period to a suspension of sodium hydride (51.10 g, 1.703 moles, Fluka N° 71614: 80% NaH in oil) in dioxane (1000 ml). This solution was stirred 90 min at room temperature. 1-Bromo-2-benzyloxy-3-chloro-propane (500 g, 1.789 moles) was added neat over a one hour period. The mixture was stirred for one hour at room temperature, followed by 24 hours at 125° C. After slow cooling to room temperature, a like quantity of sodium hydride was added neat in 5 g portions over one hour. The suspension was slowly heated to 125° C. and mechanically stirred for 120 hours at this temperature. The workup was as described in the literature references. Thus, compound 1 was first purified by distillation 172° C. at 0.6 Torr, followed by flash chromatography (tertiobutylmethylether/hexane=1/99 to 2/8) to afford 1: 382.5 g, 73.3% as a colourless oil.

EXAMPLE 2

1-Benzyloxy-3,3-bis-hydroxymethyl-cyclobutane 2

A solution of 1 (95.8 g, 313 mmoles) in dimethoxyethane (80 ml) was added dropwise at room temperature under argon to a suspension of lithium aluminum hydride (15 g, 395 mmoles) in dimethoxyethane (360 ml). The addition was done so as to maintain the reaction temperature under 50° C. (TLC control: ethyl acetate; Rf=0.30). The reaction mixture was stirred under argon at room temperature for 48 hours. After completion of the reaction, water (10 ml) was slowly added with vigorous stirring. The reaction mixture was then transferred into a 2 l flask containing silica gel (800 ml) and the solvent was removed under vacuum until a fine powder was obtained. This powder was added to a 5 cm Hyflo pad on a fritteglass and washed with ethyl acetate (400 ml fractions with TLC control). The fractions containing product were evaporated to give 55 g of crystalline 2 (79% crude). After recrystallization from ethyl-acetate/hexane 43.2 g, 62% of colourless crystals were obtained. The mother liquors were purified by flash chromatography (eluent: ethyl acetate/hexane=5/5 to 7/3) to give 5 g, 7.2% of crystals; MW=222. 285; MP=67.5–68.50° C.; I.R. (film): 3368, 3031, 2928, 2870, 1721, 1496, 1454; $^1H$ ($CDCl_3$ at 200 MHz): d in PPM: 7.30 (s: 5 $H_{ar}$); 4.40 (s: $CH_2$, Bzl); 4.06 (quint: $H_1$); 3.66 (s: $CH_2O_a$); 3.62 (s: $CH_2O_b$); 3.15 (2 OH); 2.16 (m: ABX, $H_{2a}+H_{4a}$); 1.78 (m: ABX, $H_{2b}+H_{4b}$); $^{13}C$ ($CDCl_3$ at 50 MHz): d in PPM: 138.56: $C_r$; 128.95: $C_o$; 128.45: $C_m$; 128.25: $C_p$; 71.01: $CH_2O_a$; 70.48: $CH_2O_b$; 69.43: $CH_2$, Bzl; 69.00: $C_1$; 37.35: $C_3$; 34.55: $C_2+C_4$.

Anal. calculated for $C_{13}H_{18}O_3$: C 70.25, H 8.16, O 21.60; found: C 70.09, H 8.22, O 21.64.

EXAMPLE 3

$O^5,O^{5'}$-Isopropylidene-ether of 1α-benzyloxy-3,3-bis-hydroxymethyl-cyclobutane 3

2,2-dimethoxypropane (19.9 ml, 162 mmoles) was slowly added to a solution of 2 (12 g, 54 mmoles) and p-toluenesulfonic acid (1 g) in dimethylformamide (240 ml) (TLC control: ethyl acetate; Rf=0.15). The reaction was stirred under argon at room temperature for 20 hours. Ethyl acetate (500 ml) was then added to this reaction mixture and the resulting solution was washed 4 times with brine (4×150 ml). The organic phase was dried over magnesium sulfate and evaporated to dryness to give 3, 13.7 g, 96.5% as a colourless oil which crystallized after a few days in the refrigerator. The crystals required no further purification; MW=262.350; MP=54–56° C.; I.R. (film): 3419, 3030, 2997, 2955, 2922, 2866, 2350, 1728, 1606, 1584, 1497; $^1H$ ($CDCl_3$ at 200 MHz): d in PPM (J: Hz): 7.32 (s: 5 $H_{ar}$); 4.38 (s: $CH_2$, Bzl); 4.02 (quint: J=6.5, $H_1$); 3.70 (s: $CH_2O_a$); 3.67 (s: $CH_2O_b$); 2.19 (m: ABX, J=13.5, 6.5, $H_{2a}+H_{4a}$); 1.80 (m: ABX, J=13.5, 6.5, $H_{2b}+H_{4b}$); 1.37 (s: 2 $CH_3$); $^{13}C$ ($CDCl_3$ at 50 MHz): d in PPM: 138.56: $C_r$; 128.93: $C_m$; 128.40: $C_o$; 128.20: $C_p$; 98.17: $C_{iPr}$; 70.48: $CH_2O_a$; 70.42: $CH_2O_b$; 69.26: $C_i$; 68.94: $CH_2$, Bzl; 36.54: $C_2+C_4$; 30.80: $C_3$; 24.04: 2 $CH_3$.

Anal. calculated for $C_{16}H_{22}O_3$: C 73.25, H 8.45, O 18.30; found: C 73.10, H 8.56, O 18.60.

EXAMPLE 4

$O^5,O^{5'}$-Isopropylidene-ether of 1α-hydroxy-3,3-bis-hydroxymethyl-cyclobutane 4.

Degussa palladium (2 g) in dimethoxyethane (350 ml) was first placed under a hydrogen atmosphere, 3 (44 g, 168 mmoles) was then added neat. The reaction mixture was shaken vigorously at room temperature under a hydrogen pressure of 1 atmosphere until 1 equivalent was absorbed (approximately 1 hour). After filtration of the catalyst over Hyflo, the solution was evaporated to dryness to afford 4 as a colourless syrup, 28.1 g, 97%; $C_9H_{16}O_3$: MW=172.225; I.R. (film): 3336, 2930, 2873, 1712, 1652, 1465; $^1H$ ($CDCl_3$ at 200 MHz): d in PPM: 4.20 (quint: $H_1$); 3.68 (s: $CH_2O_a$); 3.64 (s: $CH_2O_b$); 2.25 (m: ABX, $H_{2a}+H_{4a}$); 1. 65 (m: ABX, $H_{2b}+H_{4b}$); 1.35 (s: 2 $CH_3$); $^{13}C$ ($CDCl_3$ at 50 MHz): d in PPM: 98.22: $C_{iPr}$; 70.50: $CH_2O_a$; 68.79: $CH_2O_b$; 63.51: $C_1$; 39.05: $C_2+C_4$; 30.00: $C_3$; 24.02: 2 $CH_3$.

EXAMPLE 5

$O^5,O^{5'}$-Isopropylidene-ether of 1α-p-bromo-benzenesulfonyl-3,3-bis-hydroxymethyl-cyclobutane 5

A mixture of 4 (65 g, 37.8 mmoles) and triethylamine (15.8 ml, 113.2 mmoles) in dichloromethane (150 ml) was stirred under argon at 0° C. A solution of p-bromobenzenesulfonylchloride (11.57 g, 45.3 mmoles) in dichloromethane (50 ml) was slowly added at 0° C. The reaction mixture was stirred for 60 hours at room temperature (TLC control: ethyl acetate/hexane=5/5; Rf=0.5). Ethyl acetate (400 ml) was added and the solution washed 4 times with brine (4×200 ml). The organic phase was dried over magnesium sulfate and the solent evaporated. The obtained syrup was purified by flash chromatography (ethyl acetate/hexane/triethylamine=7/3/0.1 to 1/1/0.1) to afford 5, 11.4 g, 77.2% as colourless crystals; MW=391.285; MP=99–101° C.; I.R. (KBr): 2970, 2920, 2840, 1570, 1365, 1185; $^1$H (CDCl$_3$ at 200 MHz): d in PPM (J in Hz): 7.72 (m: 4 H$_{ar}$); 4.84 (quint.: J=6.9 H$_1$); 3.67 (s: CH$_2$O$_a$); 3.65 (s: CH$_2$O$_b$); 2.28 (m: ABX, H$_{2a}$+H$_{4a}$); 1.95 (m: ABX, H$_{2b}$+H$_{4b}$) 1.35 (s: 2 CH$_3$); $^{13}$C (CDCl$_3$ at 50 MHz): d in PPM: 136.44: Cr; 133.18: C$_m$; 129.77: C$_o$; 129.63: C$_p$; 98.39: C$_{iPr}$; 72.11: CH$_2$O$_a$; 69.83: CH$_2$O$_b$; 67.98: C$_1$; 36.99: C$_2$+C$_4$; 31.52: C$_3$; 23.90: 2 CH3.

Anal. calculated for C$_{15}$H$_{19}$BrSO$_5$: C 46.05, H 4.90, O 20.45, S 8.19, Br 20.42; found: C 46.09, H 5.05, O 20.32, S 8.20, Br 20.42.

EXAMPLE 6

O$^5$,O$^{5'}$-Isopropylidene-ether of 1α-adenyl-3,3-bis-hydroxymethyl-cyclobutane 6

A mixture of 5 (20 g, 51.1 mmoles), adenine (20.72 g, 153.3 mmoles) and diazabicycloundecene (23 ml, 23.34 mmoles) in dimethylsulfoxide (800 ml) were stirred under argon at 80° C. for 48 hours (TLC control: ethyl acetate/methanol=8/2, Rf=0.29; detection: 1) chlorine 2) potassium iodide). Saturated sodium bicarbonate (200 ml) and water (800 ml) were added and the solution was extracted 7 times with ethyl acetate (7×200 ml). The collected organic fractions were washed with brine (200 ml), dried over sodium sulfate and purified by flash chromatography (ethyl acetate/methanol/triethyl-amine=95/5/0.1) to afford 6, 11.1 g, 75% as colourless crystals; MW=289.339; MP=251° C. after crystallization from water/ethanol; I.R. (KBr): 3490, 3420, 3180, 2990, 2850, 2750, 1650, 1600, 1580, 1480; $^1$H (CDCl$_3$ at 200 MHz): d in PPM: 8.30 (s: H$_{2ad}$); 7.82 (s: H$_{8ad}$); 5.60 (s: NH$_2$); 4.95 (quint: H$_1$); 3.90 (s: CH$_2$O$_a$); 3.87 (s: CH2O$_b$); 2.55 (m: ABX, H$_2$+H$_4$); 1.40 (s: 2 CH$_3$); $^{13}$C (CDCl$_3$ at 50 MHz): d in PPM: 155.8: C$_{6ad}$; 152.2: C$_{2ad}$; 149.4: C$_{4ad}$; 138.8: C$_{8ad}$; 120.0: C$_{5ad}$; 97.8: C$_{iPr}$; 68.9: CH$_2$O$_a$; 66.8: CH$_2$O$_b$; 44.3: C$_1$; 39.7: C$_3$; 35.2: C$_2$; 31.3: C$_4$; 23.1: 2 CH$_3$; U.V. (water, 0.5×10$^{-4}$ mole/l): l max in nm (e max): 205 (19820), 259 (13940).

Anal. calculated for C$_{14}$H$_{19}$N$_5$O$_2$: C 58.12, H 6.62, N 24.21, O 11.06; found: C 58.18, H 6.88, N 24.19, O 11.30.

EXAMPLE 7

O$^5$,O$^{5'}$-Isopropylidene-ether of 1α-thyminyl-3,3-bishydroxymethyl-cyclobutane 7 and 1,3-bis-(O$^5$, O$^{5'}$-isopropylidene-ether of 3,3-bis-hydroxymethyl-cyclobutyl)thymine 8

A mixture of 5 (20.26 g, 51.8 mmoles), thymine (26.12 g, 207.1 mmoles) and diazabicycloundecene (31 ml, 31.5 mmoles) in dimethylsulfoxide (800 ml) were stirred under argon at 80° C. for 48 hours (TLC control: methanol/ethyl acetate=1/9; Rf=0.52 and 0.48; detection: 1) chlorine 2) potassium iodide). Saturated sodium bicarbonate (200 ml) and water (800 ml) were added and the solution was extracted 7 times with ethyl acetate (7×200 ml). The collected organic fractions were washed with brine (200 ml), dried over sodium sulfate and purified by flash chromatography (ethyl acetate/hexane/triethylamine=5/5/0.01 to 7/3/0.01) to afford fraction 1: Rf=0.47 (methanol/ethyl acetate= 1/9) compound 8, 3.85 g, 34.2%; fraction 2: Rf=0.52 (methanol/ethyl acetate=1/9) compound 7, 7.92 g, 54.6%.

O$^{5'}$,O$^{5'}$-Isopropylidene-ether of 1α-thyminyl-3,3-bis-hydroxymethyl-cyclobutane 7:

Fraction 2; MW=280.326; MP=198=201° C.; I.R. (KBr): 3190, 3000, 2950, 2860, 1680; $^1$H (CDCl$_3$ at 200 MHz): d in PPM: 9.94 (s: NH); 7.07 (s: H$_{thy}$); 4.74 (quint: H$_1$); 3.78 (s: CH$_2$O$_a$); 3.69 (s: CH$_2$O$_b$); 2.36 (m: ABX, H$_{2a}$+H$_{4a}$); 1.99 (m: ABX, H$_{2b}$+H$_{4b}$); 1.78 (s: CH$_3$ $_{thy}$); 1.35 (s: 2 CH$_3$); $^{13}$C (CDCl$_3$ at 50 MHz): d in PPM: 164.71: CO; 151.60: CO; 137.15: C$_{6thy}$; 111.12: C$_{5thy}$; 98.54: C$_{iPr}$; 69.80: CH$_2$O$_a$; 67.60: CH$_2$O$_b$; 47.21: C$_3$ $_{thy}$; 35.06: C$_2$+C$_4$; 31.66: C$_3$; 23.94: 2 CH$_3$; 12.73: CH$_3$ $_{thy}$; U.V. (methanol, 0.5×10$^{-4}$ mole/l): l max in nm: (e max): 209 (15200); 270 (18000).

Anal. calculated for C$_{14}$H$_{20}$N$_2$O$_4$: C 59.99, H 7.19, N 10.00, O 22.83; found: C 59.64, H 7.22, N 9.71, O 22.55. 1,3-Bis-(O$^5$,O$^{5'}$-isopropylidene-ether of 3,3-bishydroxymethyl-cyclobutyl)-thymine 8.

Fraction 1; MW=434.536; MP=154–155° C.; I.R. (KBr): 3000, 2940, 1610, 1570; $^1$H (CDCl$_3$ at 200 MHz): d in PPM: 7.90 (s: H$_{thy}$); 5.25 (quint: H$_1$); 5.07 (quint: H$_1$); 3.70 (s: 4 CH$_2$O); 2.42 (m: ABX, 4 H, H$_{2a}$+H$_{4a}$); 1.98 (m: ABX, 4 H, H$_{2b}$+H$_{4b}$); 1.78 (s: CH$_3$ $_{thy}$); 1.35 (s: 4 CH$_3$); $^{13}$C (CDCl$_3$ at 50 MHz): d in PPM: 168.69: CO; 163.26: CO; 157.93: C$_{6thy}$; 111.58: C$_{5thy}$; 98.16: C$_{iPr}$; 98.11: C$_{iPr}$; 68.78: CH$_2$O$_a$; 68.72: CH$_2$O$_a$; 67.70: CH$_2$O$_b$; 67.64: CH$_2$O$_b$; 53.60: C$_1$; 36.77: C$_2$; 36.72: C$_4$; 31.87: C$_3$; 31.39: C$_3$; 23.98: 2 CH$_3$; 12.06: CH$_{3thy}$; U.V. (methanol, 0.5×10$^{-4}$ mole/l): l max in nm: (e max): 215 (5520); 265 (3940).

Anal. calculated for C$_{23}$H$_{34}$N$_2$O$_6$: C 63.57, H 7.89, N 6.45, O 22.09; found: C 63.76, H 7.77, N 6.46, O 22.12.

EXAMPLE 8

1α-Adenyl-3,3-bis-hydroxymethyl-cyclobutane 9.

10 Drops of aqueous 2M hydrochloric acid were added at room temperature to a solution of 6 (1.09 g, 2.77 mmoles) in dioxane (5 ml). The solution was stirred for 1 hour, evaporated to dryness and crystallized from water. The crystals obtained were not pure as shown by TLC (chloroform/methanol/water=70/30/5), therefore the mixture of 9 and sodium chloride was purified by flash chromatography (eluent: chloroform/methanol/water=93/6/1 to 70/30/5). 9, 650 mg, 70% was obtained as colourless crystals; MW=249.275; MP=217–218° C.; I.R. (film): 3304, 3145, 2993, 2856, 1673, 1603, 1569; $^1$H (CD$_3$OD at 200 MHz): d in PPM: 8.05 (s: H$_{2ad}$); 7.95 (s: H$_{8ad}$); 4 80 (quint: H$_1$); 3.48 (s: CH$_2$O$_a$); 3.42 (s: CH$_2$O$_b$); 2.35 (m: H$_2$+H$_4$); $^{13}$C (CD$_3$OD at 50 MHz): d in PPM: 156.67: C$_{2ad}$; 143.97: C$_{8ad}$; 70.40: CH2O$_a$; 69.59: CH$_2$O$_b$; 48.27: C$_1$; 43.64: C$_3$; 37.12: C$_2$+C$_4$; U.V. (water, 0.5×10$^{-4}$ mole/l): l max in nm (e max): 194 (21200); 206 (21000); 262 (13780).

Anal. calculated for C$_{11}$H$_{15}$N$_5$O$_2$: C 53.00, H 6.07, N 28.10, O 12.84; found: C 53.05, H 6.29, N 27.87, O 12.71.

EXAMPLE 9

1,3-Bis-(3,3-bis-hydroxymethyl-cyclobutyl)-thymine-10.

10 Drops of aqueous 2M hydrochloric acid were added at room temperature to a solution of 8 (1.48 g, 3.41 mmoles) in dioxane (5 ml). Analogous to the procedure for compound 9, 10 (846 mg, 70%) was obtained as colourless crystals; MW=240.261; MP=128–130° C.; IR (film): 3346, 2934, 2870, 1604, 1575, 1435, 1329, 1293; $^1$H (CD$_3$OD at 200 MHz): d in PPM: 7.70 (s: H$_{thy}$); 5.05 (quint: H$_1$); 4.87 (quint: H$_1$); 3.44 (s: CH$_2$O$_a$); 3.42 (s: CH$_2$O$_a$); 3.38 (s: CH$_2$O$_b$); 3.36 (s: CH$_2$O$_b$); 2.15 (m: H$_{2a}$+H$_{4a}$); 1.78 (m: H$_{2b}$+H$_{4b}$); 1.76 (s: CH$_{3\ thy}$); $^{13}$C (CD$_3$OD at 50 MHz): d in PPM: 173.87: CO; 167.06: CO; 161.08: C$_{6thy}$; 115.45: C$_{5thy}$; 72.27: CH$_2$O$_a$; 71.59: CH$_2$O$_b$; 70.05: C$_1$; 69.97: C$_1$; 42.87: C$_3$; 42.66: C$_3$; 38.34: C$_2$+C$_4$; 38.19: C$_2$+C$_4$; 15.62: CH$_{3\ thy}$; U.V. (water, $0.5 \times 10^{-4}$ mole/l): 1 max in nm (e max): 268 (9640).

Anal. calculated for C$_{17}$H$_{26}$N$_2$O$_6$: C 57.61, H 7.39, N 7.90, O 27.09; found: C 57.24, H 7.38, N 7.89, O 27.12.

EXAMPLE 10

1α-Thyminyl-3,3-bis-hydroxymethyl-cyclobutane 11

10 Drops of aqueous 2M hydrochloric acid were added at room temperature to a solution of 7 (1.05 g, 3.73 mmoles) in dioxane (5 ml). Analogous to the procedure for compound 10, 11 (700 mg, 78%) was obtained as colourless crystals; MW=354.406; MP=207–208° C.; Rf=0.23, methanol/ethyl acetate=1/9; I.R. (KBr): 3170, 3040, 2990, 2950, 2870, 1690, 1660; $^1$H (CD$_3$OD at 400 MHz): d in PPM (J: Hz): 7.33 (q: H$_{thy}$); 4.72 (quint: J: 8.5, H$_1$); 3.47 (s: CH$_2$O$_a$); 3.37 (s: CH$_2$O$_b$); 2.07 (d: J: 8.5, H$_2$+H$_4$); 1.78 (s: CH$_{3\ thy}$); $^{13}$C (CD$_3$OD at 50 MHz): d in PPM: 176: CO; 167: CO; 142.29: CH$_{thy}$; 70.45: CH$_2$O$_a$; 69.84: CH$_2$O$_b$; 49.68: C$_1$; 43.2: C$_3$; 35.77: C$_2$+C$_4$; 16.27: CH$_{3\ thy}$; U.V. (water, $0.5 \times 10^{-4}$ mole/l): 1 max in nm (e max): 211 (8840); 274 (10520).

Anal. calculated for C$_{11}$H$_{16}$N$_2$O$_4$: C 54.99, H 6.71, N 11.66, O 26.64; found: C 54.86, H 6.74, N 11.65, O 26.56.

EXAMPLE 11

1α-Thyminyl-3β-hydroxymethyl-3α-methoxytrityloxymethyl-cyclo-butane 12 and 1α-thyminyl-3α-hydroxymethyl-3β-methoxytrityloxymethyl-cyclobutane 13

11 (314 mg, 1.307 mmoles) was evaporated 3 times with pyridine (3×10 ml). Methoxytritylchloride (316.5 mg, 1.03 mmoles) was added under argon to a solution of 11 in pyridine (10 ml). The reaction was stirred at room temperature for 8 hours (TLC control: ethyl acetate/hexane=8/2). More methoxytritylchloride (100 mg, 0.32 mmoles) was added in two portions after 5 hours. The reaction mixture was stirred 15 hours at room temperature. Five spots were visible on TLC (chloroform/methanol/triethylamine=95/5/1; spot 1: Rf=0.99, degradation product of methoxytritylchloride; spot 2: Rf=0.95, bis-methoxytrityl-derivative; spot 3: Rf=0.40, compound 12; spot 4: Rf=0.35, compound 13; spot 5: Rf=0.05, unreacted diol 11. Other experiments have shown that adding more methoxytritylchloride did not diminish the amount of unreacted diol 11 but increased the amount of bis-methoxytrityl-derivative. Sodium bicarbonate (10 ml, 1M) was added, the solution extracted 4 times with ethyl acetate (4×20 ml) and the organic phase dried over sodium sulfate. These products were separated by flash chromatography (eluent: chloro-form/acetone/triethylamine=99/1/1 slowly to 80/20/1) to give fraction 1: 70 mg (8.9%); fraction 2, 12: 234 mg (34.9%); fraction 3, 13: 281 mg (41.9%); fraction 4, 11: 20 mg (6.4%).

1α-Thyminyl-3,3-bis-methoxytrityloxymethyl-cyclobutane: C$_{51}$H$_{48}$N$_2$O$_6$: MW=784.954; fraction 1; Rf=0.95, chloroform/methanol/triethylamine=95/5/1 ; 70 mg (8.9%).

1α-Thyminyl-3β-hydroxymethyl-3β-methoxytrityloxymethyl-cyclobutane 12:

Fraction 2; Rf=0.40, chloroform/methanol/triethylamine= 95/5/1; 234 mg (34.9%); MW=512.608; MP=126° C.; $^1$H (CDCl$_3$ at 400 MHz): d in PPM (J: Hz): 8.25 (s: NH); 7.43 (m: 4 H$_{ar}$); 7.31 (dd: 6 H$_{ar}$); 7.25 (m: 2 H$_{ar}$); 7.13 (q: J=1.5; H$_{thy}$); 6.85 (d: 2 H$_{ar}$); 4.94 (quint: J: 9.0; H$_1$); 3.78 (s: CH$_3$O); 3.72 (d: J: 4.5; CH$_2$OH); 3.24 (s: CH$_2$OTrOMe); 2.31 (ddd: ABX J: 3.0, 9.0, 11.0; H$_{2a}$+H$_{4a}$); 2.10 (ddd: ABX J: 3.0, 9.0, 10.2; H$_{2b}$+H$_{4b}$); 2.01 (t: J: 4.5; OH); 1.72 (d: J: 1.5; CH$_{3\ thy}$); $^1$H (CDCl$_3$ at 400 MHz) NOE experiments: Irradiation on H$_1$: positive NOE on CH$_2$OH, H$_{2b}$+H$_{4b}$ and no effect on H$_{2a}$+H$_{4a}$; irradiation on CH$_2$OH: positive NOE on H$_1$ and H$_{2b}$+H$_{4b}$; irradiation on CH$_2$OTrOMe: positive NOE on CH$_2$OH, H$_{2a}$+H$_{4a}$ and no effect on HM; irradiation on H$_{2a}$+H$_{4a}$: positive NOE on H$_{2b}$+H$_{4b}$, CH$_2$OTrOMe and no effect on H$_1$; irradiation on H$_{2b}$+H$_{4b}$: positive NOE on H$_{2a}$+H$_{4a}$, H$_1$, CH$_2$OH and no effect on CH$_2$OTrOMe; U.V. (methanol, $0.5 \times 10^{-4}$ mole/l): 1 max in nm (e max): 274 (10720) FAB-MS: 513=MH$^+$; 535=M+Na; 435=M–Ph; 273=MeOTr$^+$; 241=M–TrOMe$^+$; 195=MeOTr–Ph$^+$; 165= MeOTr–PhOMe$^+$; 127=Thy +H$^+$ Anal. calculated for C$_{31}$H$_{32}$N$_2$O$_5$+0.42 H$_2$O: C 71.58, H 6.36, N 5.39, O 16.67; found: C 71.58, H 6.37, N 5.46, O 16.72.

1α-Thyminyl-3α-hydroxymethyl-3β-methoxytrityloxymethyl-cyclobutane 13:

Fraction 3: Rf=0.35, chloroform/methanol/triethylamine= 95/5/1; 281 mg (41.9%); MW=512.608; MP=120° C.; $^1$H (CDCl$_3$ at 400 MHz): d in PPM (J: Hz): 8.25 (s: NH); 7.43 (m: 4 H$_{ar}$); 7.36 (q: J=1.5; H$_{thy}$); 7.31 (m: 6 H$_{ar}$); 7.23 (m: 2 H$_{ar}$); 6.86 (m: 2 H$_{ar}$); 4.81 (quint: J=8.5; H1); 3.82 (s: CH$_3$O); 3.64 (d: J=3.5; CH$_2$OH); 3.26 (s: CH$_2$OTrOMe); 2.28 (m: A$_2$X; H$_2$+H$_4$); 2.06 (t: J=3.7; OH); 1.94 (d: J=1.5; CH$_{3\ thy}$); $^1$H (CDCl$_3$ at 400 MHz) NOE experiments: irradiation on H$_1$: positive NOE on CH$_2$OTrOMe and H$_2$+H$_4$; irradiation on CH$_2$OH: positive NOE on CH$_2$OTrOMe, H$_2$+H$_4$ and no effect on H$_1$; irradiation on CH$_2$OTrOMe: positive NOE on H$_1$, H$_2$+H$_4$ and CH$_2$OH; U.V. (methanol, $0.5 \times 10^{-4}$ mole/l): 1 max in nm (e max): 274 (10740); FAB-MS: 513=M+H$^+$; 535=M+Na; 435=M–Ph; 241=M–TrOMe; 273=MeOTr$^+$; 241=M–TrOMe$^+$; 195=MeOTr–Ph$^+$; 165=MeOTr–PhOMe$^+$; 127=Thy+H$^+$.

Anal. calculated for C$_{31}$H$_{32}$N$_2$O$_5$+0.50 H$_2$O: C 71.38, H 6.38, N 5.37, O 16.87; found: C 71.26, H 6.48 N 5.44, O 16.65.

EXAMPLE 12

O$^5$,O$^{5'}$-Isopropylidene-ether of 1α-(N, N-dibenzoyladenyl)-3,3-bis-hydroxymethyl-cyclobutane 16

A pyridine solution of 6 (707 mg, 2.44 mmoles) was evaporated 3 times to dryness (3×15 ml). Benzoyl chloride (700 ml, 6.02 mmoles) was added neat dropwise to a solution of 6 in pyridine (5 ml). The reaction mixture was stirred 15 hours at room temperature (TLC control: methanol/ethyl acetate=2/8, Rf=0.55). Water (20 ml) was added and the solution extracted twice with ethyl acetate (2×40 ml). The organic phase was dried over sodium sulfate and evaporated to dryness. The compound was crystallized from chloroform/methanol to afford 16 (1.205 g, 99%) as colourless crystals; MW=494.533; MP=221–222° C. after crystallization from chloroform/methanol; I.R. (KBr): 3060, 2990, 2930, 2850, 1700, 1600; $^1$H (CDCl$_3$ at 200 MHz): d in PPM: 8.64 (s: H$_{2ad}$); 8.08 (s: H$_{8ad}$); 7.85 (d: H$_{o\ PhCO}$);

7.48 (t: $H_{p\ PhCO}$); 7.33 (m: $H_{m\ PhCO}$); 5.03 (quint: $H_1$); 3.92 (s: 2 $CH_2O$); 2.63 (d: $H_2+H_4$); 1.42 (s: 2 $CH_3$); $^{13}C$ ($CDCl_3$ at 50 MHz): d in PPM: 172.94: CO ; 164.00: $C_{6ad}$; 152.43: $C_{2ad}$; 144.14: $C_{8ad}$; 141.80: $C_{4ad}$; 134.64: $C_{r\ PhCO}$; 134.09: $C_{p\ PhCO}$; 133.52: $C_{p\ PhCO}$; 130.66: $C_{o\ PhCO}$; 130.02: $C_{o\ PhCO}$; 129.24: $C_{m\ PhCO}$; 128.95: $C_{m\ PhCO}$; 112.80: $C_{5ad}$; 98.56: $C_{iPr}$; 69.90: $CH_2O_a$; 67.79: $CH_2O_b$; 55.02: $C_1$; 45.83: $C_3$; 35.80: $C_2$; 32.24: $C_4$; 24.01: $CH_3$; U.V. (methanol, $0.5 \times 10^{-4}$ mole/l): l max in nm (e max): 249 (21700).

Anal. calculated for $C_{28}H_{24}N_5O_4$: C 67.59, H 5.47, N 14.08, O 12.86, found: C 67.60, H 5.50, N 14.10, O 12.90.

EXAMPLE 13

$O^5,O^{5'}$-Isopropylidene-ether of 1α-(N-benzoyl-adenyl)-3,3-bis-hydroxymethyl-cyclobutane 17

Concentrated ammonia (3 ml, 29%) was added dropwise to a solution of 16 (718 mg, 1.47 mmoles) in THF (7.3 ml) and water (1.5 ml). The reaction mixture was stirred 4 hours at room temperature (TLC control): 4 spots were visible: spot 1: Rf=0.46, ethyl acetate; Rf=0.54, ethyl acetate/methanol=9/1, $PhCONH_2$; spot 2: Rf=0.36, ethyl acetate; Rf=0.45, ethyl acetate/methanol =9/1, compound 16; spot 3: Rf=0.10, ethyl acetate; Rf=0.42, ethyl acetate/methanol=9/1, compound 17; spot 4: Rf=0.02, ethyl acetate; Rf=0.26, ethyl acetate/methanol=9/1, $PhCOO^-NH_{4+}$. Water (20 ml) was added and the solution extracted 4 times with ethyl acetate (2×40 ml). The organic phase was dried over sodium sulfate and evaporated to dryness. These compounds were separated by flash chromatography (eluent: ethyl acetate/hexane=5/5 to ethyl acetate/methanol=8/2); MW=393.448; MP=180–182° C. after crystallization from ethyl acetate/hexane; I.R. (film): 3500–3100, 2991, 2941, 2856, 1695, 1613; $^1H$ ($CDCl_3$ at 200 MHz): d in PPM: 9.75 (s: NH); 8.23 (s: $H_{2ad}$); 8.08 (s: $H_{8ad}$); 8.02 (d: $H_{o\ PhCO}$); 7.48 (m: $H_{p\ PhCO}+H_{m\ PhCO}$); 5.02 (quint: $H_1$); 3.43 (s: 2 $CH_2O$); 2.57 (d: $H_2+H_4$); 1.47 (s: 2 $CH_3$); $^{13}C$ ($CDCl_3$ at 50 MHz): d in PPM: 165.84: C=O; 152.54: $C_{2ad}$; 152.37: $C_{6ad}$; 150.26: $C_{4ad}$; 142.17: $C_{8ad}$; 134.15: $C_{r\ PhCOb}$ 132.94: $C_{p\ PhCO}$; 128.95: $C_{m\ PhCO}$; 128.55: $C_{o\ PhCO}$; 123.91: $C_{5ad}$; 98.45: $C_{iPr}$; 69.71: $CH_2O_a$; 67.76: $CH_2O_b$; 62.64: $C_1$; 45.71: $C_3$; 35.88: $C_2$; 32.26: $C_4$; 24.01: $CH_3$; U.V. (methanol, $0.5 \times 10^{-4}$ mole/l): l max in nm: (e max): 281 (20180).

Anal. calculated for $C_{21}H_{23}N_5O_3$: C 64.11, H 5.89, N 17.80, O 12.20; found: C 64.07, H 6.04, N 17.33, O 12.47

EXAMPLE 14

1α-(N,N-Dibenzoyl-adenyl)-3α-hydroxymethyl-3β-methoxytrityloxymethyl-cyclobutane 19 and 1α-(N,N-dibenzoyl-adenyl)-3β-hydroxymethyl-3α-methoxytrityloxymethyl-cyclobutane 20

Aqueous 4M hydrochloric acid (10 drops) was added to a solution of 16 (209.5 mg, 0.421 mmoles) in dioxane (5 ml). The reaction mixture was stirred at room temperature for 5 hours (TLC control: dichloromethane/methanol=9/1) and neutralized with pyridine. This compound 18, 1α-(N,N-dibenzoyl-adenyl)-3,3-bis-hydroxymethyl-cyclobutane, was not stable and could not be stored in the refrigerator. First a pyridine solution of 18 was evaporated 3 times to dryness (3×10 ml), then methoxy- tritylchloride (130 mg, 0.421 mmole) was added in one portion to the pyridine solution (5 ml) of 18 in the presence of dimethylaminopyridine (20 mg). The reaction mixture was stirred 15 hours at room temperature (TLC control: 2 runs with 2 different solvents 1: tertiobuty-1-methylether/hexane=20/80; 2.: tertiobutylmethylether/ethanol=80/20) Five spots were visible on TLC: spot 1, Rf=0.61, degradation product of methoxytritylchloride; spot 2, Rf=0.48, bis-methoxytrityl-derivative; spot 3, Rf=0.44, methoxytrityl-derivative; spot 4, Rf=0.39, methoxytrityl-derivative; spot 5, Rf=0.21, unreacted diol. Water (20 ml), sodium bicarbonate (1M, 20 ml) and ethyl acetate (50 ml) were added. The aqueous phase was extracted 3 more times with ethyl acetate (3×50 ml), dried over sodium sulfate and evaporated to dryness. These compounds were separated by flash chromatography (eluent: tertiobutylmethylether/hexane=2/8 to tertiobutylmethylether/methanol:=2/8) to give fraction 1: Rf=0.48, 40 mg, 9.5%; fraction 2: Rf=0.44, compound 19, 46 mg, 15.0%; fraction 3: Rf=0.39, compound 20, 46 mg, 15.0%; fraction 4: Rf=0.21, compound 18, 30 mg, 14.3%.

1α-(N,N-Dibenzoyl-adenyl)-3,3-bis-methoxytrityloxymethyl-cyclobutane:

Fraction 1, $C_{65}H_{55}N_5O_6$ MW=1002.185; $^1H$ ($CDCl_3$ at 200 MHz): d in PPM: 8.62 (s: $H_{2ad}$); 8.22 (s: $H_{8ad}$); 7.85 (m: $H_{o\ PhCO}$); 7.50–>7.20 (m: 30 $H_{ar}$); 6.82 (m: 4 $H_{ar}$); 4.96 (quint: $H_1$); 3.78 (s: $CH_3O$); 3.72 (s: $CH_3O$); 3.35 (s: $CH_2O_a$); 3.30 (s: $CH_2O_b$); 2.50 (m $A_2X$: $H_2+H_4$).

1α-(N,N-Dibenzoyl-adenyl)-3α-hydroxymethyl-3β-methoxytrityloxymethyl-cyclobutane 19:

Fraction 2, $C_{45}H_{39}N_5O_5$; MW=729:838; $^1H$ ($CDCl_3$ at 200 MHz): d in PPM: 8.63 (s: $H_{2ad}$); 8.24 (s: $H_{8ad}$); 7.85 (m: 4 $H_{ar}$); 7.50–>7.20 (m: 18 $H_{ar}$); 6.82 (m: 2 $H_{ar}$); 4.98 (quint: $H_1$); 3.80 (s: $CH_3O$); 3.70 (s: $CH_2OH$); 3.30 (s: $CH_2OTrOMe$); 2.80 (m ABX: $H_{2a}+H_{4a}$); 2.50 (m ABX: $H_{2b}+H_{4b}$); $^{13}C$ ($CDCl_3$ at 50 MHz): d in PPM: 172.97: 2 CO; 159.30: $C_{6ad}$; 153.79: $C_{p\ PhOMe}$; 152.34: $C_{2ad}$; 152.27: $C_{4ad}$; 144.66: $C_{8ad}$; 144.31: $C_{r\ Ph}$; 135.78: $C_{r\ PhOMe}$; 134.69: $C_{r\ phCO}$; 133.49: $C_{p\ PhCO}$; 130.84: $C_{o\ PhOMe}$; 130.00: $C_{o\ PhCO}$; 129.23: $C_{m\ PhCO}$; 128.87: $C_{m\ Ph}$; 128.51: $C_{o\ Ph}$; 127.65: $C_{p\ Ph}$; 113.82: $C_{5ad}$; 113.75: $C_{m\ PhOMe}$; 69.55: $CH_2O_a$; 67.62: $CH_2O_b$; 55.58: $C_1$; 45.94: $C_3$; 38.44: $C_2$; 34.39: $C_4$.

1α-(N,N-Dibenzoyl-adenyl)-3β-hydroxymethyl-3α-methoxytrityloxymethyl-cyclobutane 20:

Fraction 3, $C_{45}H_{39}N_5O_5$, MW=729:838; $^1H$ ($CDCl_3$ at 200 MHz): d in PPM: 8.55 (s: $H_{2ad}$); 8.04 (s: $H_{8ad}$); 7.87 (m: 4 $H_{ar}$); 7.50–>7.20 (m: 18 $H_{ar}$); 6.80 (m: 2 $H_{ar}$); 5.06 (quint: $H_1$); 3.80 (s: $CH_2OH$); 3.76 (s: $CH_3O$); 3.46 (s: $CH_2OTrOMe$); 2.55 (m $A_2X$: $H_2+H_4$).

EXAMPLE 15

1α-(N-Benzoyl-adenyl)-3,3-bis-hydroxymethyl-cyclobutane 21

Aqueous 4M hydrochloric acid (200 ml) was added to a solution of 17 (1.00 g, 2.54 mmoles) in dioxane (10 ml) and water (1 ml). This mixture was stirred at room temperature for 5 hours (TLC control: ethyl acetate/methanol=7/3), after the reaction was complete the solution was neutralized with solid sodium bicarbonate and evaporated to dryness. The obtained oil was purified by flash chromatography (eluent: ethyl acetate to ethyl acetate/methanol=8/2) to afford 21 (700 mg, 78%) as colourless crystals. This compound was not very stable and could not be stored in the freezer for a longer time; $C_{18}H_{19}N_5O_3$; MW=353.383; $^1H$ ($CD_3OD$ at 200 MHz): d in PPM: 9.00 (s: $H_{2ad}$); 8.70 (s: $H_{8ad}$); 7.80 (d: $H_{o\ PhCO}$); 7.55 (dd: $H_{p\ PhCO}$); 7.35 (t: $H_{m\ PhCO}$); 5.08 (quint: $H_1$); 3.70 (s: $CH_2O_a$); 3.58 (s: $CH_2O_b$); 2.50 (d: $H_2+H_4$); $^{13}C$ ($CD_3OD$ at 50 MHz): d in PPM: 171.80: CO; 154.22: $C_{6ad}$; 152.52: $C_{2ad}$; 149.14: $C_{4ad}$; 146.58: $C_{8ad}$; 136.87: $C_{r\ PhCO}$; 133.81: $C_{p\ PhCO}$; 131.62: $C_{m\ PhCO}$; 131.03: $C_{o\ PhCO}$; 120.81: $C_{5ad}$; 67.88: $CH_2O_a$; 66.55: $CH_2O_b$; 48.54: $C_1$; 41.85: $C_3$; 34.88: $C_2+C_4$.

EXAMPLE 16

1α-(N-Benzoyl-adenyl)-3α-hydroxymethyl-3β-methoxytrityloxymethyl-cyclobutane 22 and 1α-(N-benzoyl-adenyl)-3β-hydroxymethyl-3α-methoxytrityloxymethyl-cyclobutane 23

Methoxytritylchloride (481 mg, 1.56 mmoles) was added under argon in 100 mg portions every 2 hours to a solution of 17 (500 mg, 1.41 mmoles) in pyridine (5 ml) in the presence of dimethylaminopyridine (100 mg). The reaction mixture was stirred at room temperature for 15 hours (TLC control: ethyl acetate/methanol=8/2) Five spots were visible on TLC: spot 1: Rf=0.95, degradation product of methoxytrityl-chloride; spot 2: Rf=0.80, bis-methoxytrityl-derivative; spot 3: Rf=0.40, methoxytrityl-derivative; spot 4: Rf=0.35, methoxytrityl-derivative; spot 5: Rf=0.10, unreacted diol. Two more additions of methoxytritylchloride (2×100 mg) did not show further reaction. Water (1 ml) was added, the solution extracted 6%imes with ethyl acetate (6×15 ml), dried over sodium sulfate and evaporated to dryness. The mixture was separated by flash chromatography (eluent: ethyl acetate/hexane=1/1%o ethyl acetate/methanol=7/3) to afford: fraction 1: 100 mg, 8% bis-methoxytrityl-derivative; fraction 2: 240 mg, 27% methoxytrityl-β-derivative 22; fraction 3: 80 mg, 9% methoxytrityl-α-derivative 23; fraction 4: 50 mg, 10% unreacted diol 17.

1α-(N-Benzoyl-adenyl)-3,3-bis-methoxytrityloxymethyl-cyclobutane:

Fraction 1, $C_{56}H_{51}N_5O_5$, MW=874.054; $^1H$ (CDCl$_3$ at 200 MHz): d in PPM: 9.55 (s: NH); 8.70 (s: $H_{2ad}$); 8.05 (d: 2 $H_{ar}$); 7.95 (s: $H_{8ad}$); 7.45 (m: 10 $H_{ar}$); 7.25 (m: 17 $H_{ar}$); 6.85 (m: 4 $H_{ar}$); 4.95 (quint: $H_1$); 3.75 (s: 2 $CH_3O$); 3.47 (s: $CH_2O_a$); 3.42 (s: $CH_2O_b$); 2.55 (m: $H_2+H_4$).

1α-(N-Benzoyl-adenyl)-3α-hydroxymethyl-3β-methoxytrityloxymethyl-cyclobutane 22:

Fraction 2, MP=194° C.; I.R. (film): 3396, 2935, 1700, 1611, 1581, 1508, 1453; $^1H$ (CDCl$_3$ at 360 MHz): d in PPM: 9.10 (s: NH); 8.79 (s: $H_{2ad}$); 8.12 (s: $H_{8ad}$); 8.05 (d: $H_{o\ PhCO}$); 7.61 (t: $H_{p\ PhCO}$); 7.53 (t: 2 $H_{ar}$); 7.49 (d: 4 $H_{ar}$); 7.39->7.25 (m: 8 $H_{ar}$); 6.90 (d: $H_{m\ PhOMe}$); 4.98 (quint: $H_1$); 3.83 (s: $CH_3O$); 3.76 (s: $CH_2OH$); 3.32 (s: $CH_2OTrOMe$); 2.90 (m: ABX, $H_{2a}+H_{4a}$); 2.52 (m: ABX, $H_{2b}+H_{4b}$); $^{13}C$ (CDCl$_3$ at 50 MHz): d in PPM: 165.29: CO; 159.16: $C_{6ad}$; 152.61: $C_{2ad}$; 152.55: $C_{p\ PhOMe}$; 150.80: $C_{4ad}$; 144.71: $C_{8ad}$; 142.65: $C_{r\ Ph}$; 135.70: $C_{r\ PhOMe}$; 134.16: $C_{r\ PhCO}$; 133.20: $C_{p\ PhCO}$; 130.95: $C_{m\ PhCO}$; 129.28: $C_{o\ PhCO}$; 128.88: $C_{m\ Ph}$; 128.44: $C_{o\ Ph}+C_{o\ PhOMe}$; 127.58: $C_{p\ Ph}$; 123.50: $C_{5ad}$; 113.71: $C_{m\ PhOMe}$; 67.77: $CH_2O_a$; 67.29: $CH_2O_b$; 55.77: $C_1$; 45.36: $C_3$; 39.32: $C_2$; 33.68: $C_4$; $^1H$ (CDCl$_3$ at 360 MHz) NOE experiments: irradiation on $H_1$: positive NOE on $CH_2OTrOMe$, $H_{2b}$ $H_{2b}+H_{4b}$, $H_{8ad}$ and no effect on $CH_2OH$, irradiation on $CH_2OTrOMe$: positive NOE on $CH_2OH$ and on $H_1$; U.V. (ethanol, $0.5×10^{-4}$ mole/l): 1 max in nm (e max): 231 (22740); 281 (17060); $C_{37}H_{35}N_5O_4$: MW: 625.730. FAB-MS: 626=MH$^+$; 522=M−PhCO; 352=M−TrOMe; 273=MeOTr$^+$; 240=PhCONH-A-dH$^+$.

1α-(N-Benzoyl-adenyl)-3β-hydroxymethyl-3α-methoxytrityloxymethyl-cyclobutane 23:

Fraction 3, MP=112° C.; $^1H$ (CDCl$_3$ at 360 MHz): d in PPM: 9.16 (s: NH); 8.73 (s: $H_{2ad}$); 8.05 (d: $H_{o\ PhCO}$); 7.98 (s: $H_{8ad}$); 7.47->7.15 (m: 13 $H_{ar}$); 6.87 (d: $H_{m\ PhOMe}$); 5.10 (quint: $H_1$); 3.85 (s: $CH_2OH$); 3.72 (s: $CH_3O$); 3.33 (s: $CH_2OTrOMe$); 2.53 (d: $H_2+H_4$); $^{13}C$ (CDCl$_3$ at 50 MHz): d in PPM: 165.30: CO; 159.12: $C_{6ad}$; 150.80: $C_{2ad}$; 150.40: $C_{p\ PhOMe}$; 148.00: $C_{4ad}$; 142.05: $C_{8ad}$; 135.83: $C_{r\ PhOMe}$; 134.29: $C_{r\ PhCO}$; 133.13: $C_{p\ PhCO}$; 130.81: $C_{m\ PhCO}$; 129.19: $C_{o\ PhCO}$; 128.89: $C_{m\ Ph}$; 128.54: $C_{o\ Ph}$; 128.43: $C_{o\ PhOMe}$; 127.58: $C_{p\ Ph}$; 123.52: $C_{5ad}$; 113.70: $C_{m\ PhOMe}$; 68.82: $CH_2O_a$; 67.19: $CH_2O_b$; 55.72: $C_1$; 45.77: $C_3$; 38.95: $C_2$; 34.53: $C_4$; $^1H$ (CDCl$_3$ at 360 MHz) NOE experiments: irradiation on $H_1$: positive NOE on $CH_2OH$, $H_2+H_4$, $H_{8ad}$ and no effect on $CH_2OTrOMe$; irradiation on $CH_2OTrOMe$: positive NOE on $CH_2OH$, $H_2+H_4$ and no effect on $H_1$, irradiation on $CH_2OH$: positive NOE on $CH_2OTrOMe$, $H_2+H_4$, OH and $H_1$, U.V. (ethanol, $0.5×10^{-4}$ mole/l): 1 max in nm (e max): 230 (24880); 281 (18040); $C_{37}H_{35}N_5O_4$, MW=625.730, FAB-MS: 626=MH$^+$; 522=M−PhCO; 352=MeOTr$^+$; 273=MeOTr$^+$; 240=PhCONH-AdH$^+$.

EXAMPLE 17

1α-(N-Benzoyl-adenyl)-3α-hydroxymethyl-3α-methoxytrityloxymethyl-cyclobutane 22

Concentrated aqueous ammonia (200 ml) was added to a solution of 19 (200 mg, 0.274 mmole) in tetrahydrofuran (2 ml) and water (500 ml). This mixture was stirred at room temperature for 5 hours (TLC control: ethyl acetate/methanol=8/2) and evaporated to dryness. The obtained oil was purified by flash chromatography (eluent: ethyl acetate to ethyl acetate/methanol=7/3) to afford 100 mg, 59% of colourless crystals.

EXAMPLE 18 p 1α-(N-Benzoyl-adenyl)-3β-hydroxymethyl-3α-methoxytrityloxymethyl-cyclobutane 23:

Analogous to the procedure for 22, 20 (200 mg, 0.274 mmole) afforded 23 (100 mg, 59%) as colourless crystals.

EXAMPLE 19

1α-Benzyloxy-3-bis-carboxy-cyclobutane 26

4M aqueous potassium hydroxide (77.4 ml, 309.6 mmoles) was added to a solution of 4 (23.71 g, 77.39 mmoles) in water (57 ml) and ethanol (171 ml). The reaction mixture was stirred at reflux for 5 hours and evaporated to dryness. The residue (approximately 21 g) was brought to $P_H$=3 with 2M aqueous hydrochloric acid (approximately 160 ml). Ethyl acetate (150 ml) was added and the aqueous phase extracted 4 times with ethyl acetate (4×150 ml). The organic phase was dried over sodium sulfate and evaporated to dryness. The oily residue was twice evaporated with toluene (2×100 ml), the diacid 26 crystallized; $C_{13}H_{14}O_5$; MW=250.254, yellow crystals, MP=160–162° C.; I.R. (film): 3470, 2926, 2856, 1728, 1497, 1453; $^1H$ (DMSO at 200 MHz): d in PPM: 7.32 (s: 5 $H_{ar}$); 4.98 (s: COOH); 4.45 (s: $CH_2$, Bzl); 4.15 (quint: $H_1$); 2.75 (m: ABX, $H_{2a}+H_{4a}$); 2.45 (m: ABX, $H_{2b}+H_{4b}$); $^{13}C$ (DMSO at 50 MHz): d in PPM: 176.10: CO; 175.60: CO; 139.78: $C_r$; 129.72: $C_o$; 129.66: $C_m$; 129.38: $C_p$; 71.49: $C_1$; 69.33: $CH_2$, Bzl; 47.25: $C_3$; 39.08: $C_2+C_4$.

EXAMPLE 20

1α-Benzyloxy-3α-carboxy-cyclobutane 27 cis and 1α-benzyloxy-3β-carboxy-cyclobutane 27 trans:

The diacid 26 was decarboxylated in a kugelrohr distillation apparatus at 215° C. and 0.4 Torr. A 1:1 mixture of the two monoacids 27 cis and 27 trans was obtained. At this stage both isomers could not be separated by flash chromatography (1 spot on TLC for both compounds: chloroform/methanol/water=65/30/5): 27 cis+27 trans: 14.69 g, 88.6% starting from diester 4; $C_{14}H_{14}O_2$: MW: 214.265; I.R. (film): 3200, 2926, 2854, 2350, 1732, 1603, 1496, 1454; $^1$H (CDCl$_3$ at 200 MHz): d in PPM: 11.40 (s: COOH); 7.35 (s: 5 $H_{ar}$); 4.45 (s: $CH_2$, Bzl); 4.35 (quint: $H_1$); 3.98 (quint: $H_1$); 3.10 (m: $H_3$); 2.68 (m: $H_3$); 2.55 (m: ABX, $H_{2a}$+$H_{4a}$); 2.35 (m: ABX, $H_{2b}$+$H_{4b}$); $^{13}$C (CDCl$_3$ at 50 MHz): d in PPM: 182.85: CO; 181.13: CO; 138.51: $C_r$; 138.45: $C_r$; 129.00: $C_o$; 128.45: $C_m$; 128.33: $C_p$; 71.78: $C_1$; 70.70: $CH_2$, Bzl; 70.52: $CH_2$, Bzl; 68.78: $C_1$; 34.24: $C_2$; 34.13: $C_2$; 33.60: $C_4$; 33.46: $C_4$; 31.95: $C_3$; 29.56: $C_3$.

EXAMPLE 21

1α-Benzyloxy-cyclobutane-3α-carboxylic acid chloride 28 cis and 1α-benzyloxy-cyclobutane-3β-carboxylic acid chloride 28 trans:

Neat oxalyl chloride (42.3 ml, 485 mmoles) was added slowly over 1 hour at 0° C. to a solution of 27 cis+27 trans (28.61 g, 133.5 mmoles) in carbon tetrachloride (230 ml). The reaction started immediately with evolution of $CO_2$. The mixture was stirred 1 hour at 0° C. and 12 hours at room temperature. This solution was evaporated to dryness to afford a 1:1 mixture of 28 cis+28 trans: 31.13 g, 99.5%; $C_{12}H_{13}ClO_2$; MW=234.363; $^1$H (CDCl$_3$ at 200 MHz): d in PPM: 7.35 (s: 5 $H_{ar}$.); 4.48 (s: $CH_2$, Bzl); 4.42 (s: $CH_2$, Bzl); 4.22 (quint: $H_1$); 3.98 (quint: $H_1$); 3.55 (m: $H_3$); 3.08 (m: $H_3$); 2.68 (m: ABX, $H_{2a}$+$H_{4a}$); 2.35 (m: ABX, $H_{2b}$+$H_{4b}$); $^{13}$C (CDCl$_3$ at 50 MHz): d in PPM: 157.00: CO; 156.22: CO; 138.17: $C_r$; 138.14: $C_r$; 129.09: $C_o$; 128.79: $C_o$; 128.61: $C_m$; 128.52: $C_m$; 128.12: $C_p$; 70.93: $C_1$; 70.70: $CH_2$, Bzl; 67.72: $C_1$; 44.37: C3; 41.86: C3; 35.14: $C_2$; 34.08: $C_4$.

EXAMPLE 22

1α-Benzyloxy-3α-carbethoxy-cyclobutane 29 cis and 1α-benzyloxy-3β-carbethoxy-cyclobutane 29 trans:

The 1:1 mixture of the acid chlorides 28 cis and 28 trans (31.13 g, 132.8 mmoles) was twice evaporated in the presence of carbon tetrachloride (50 ml) and toluene (50 ml). Ethanol (100 ml) was slowly added at 0° C. under argon to the solution of 28 cis and 28 trans in carbon tetrachloride (50 ml). The reaction mixture was stirred for 5 hours at room temperature (TLC control: tertiobutylmethylether/hexane=2/8) and evaporated to dryness. The isomeric ethyl esters were separated by flash chromatography (eluent: tertiobutylmethylether/hexane=2/8 to 8/2). The fraction containing both isomers was chromatographed a second time with the same solvent to give fraction 1: Rf=0.28, compound 29 trans, 12.02 g, 38.4% and fraction 2: Rf=0.22, compound 29 cis, 11.94 g, 38.2% starting from the mixture of monoacids 27 cis and 27 trans.

1α-Benzyloxy-3β-carbethoxy-cyclobutane 29 trans:

Fraction 1, MW=234.296; IR (film): 2986, 2945, 1731, 1604, 1496, 1374, 1354; $^1$H (CDCl$_3$ at 400 MHz): d in PPM: 7.35 (s: Ph); 4.48 (s: $CH_2$, Bzl); 4.32 (quint: $H_1$); 4.18 (q: $CH_2$, Et); 3.08 (tt: $H_3$); 2.55 (m: $H_{2b}$+$H_{4b}$); 2.35 (m: $H_{2a}$+$H_{4a}$); 1.35 (t: $CH_3$, Et); $^{13}$C (CDCl$_3$ at 100 MHz): d in PPM: .176.8: CO; 138.0: $C_{r\,Ph}$; 128.2: $C_{o\,Ph}$; 127.6: $C_{m\,Ph}$; 127.5: $C_{p\,Ph}$; 71.5: $C_1$; 70.4: $CH_2$, Bzl; 60.2: $CH_2$, Et; 33.4: $C_2$+$C_4$; 32.0: $C_3$; 14.1: $CH_3$, Et; $^1$H (CDCl$_3$ at 400 MHz) NOE experiments: irradiation on $H_{2b}$: positive NOE on $H_1$ and no effect on $H_3$ and Et; irradiation on $H_{2a}$: positive NOE on $H_3$, Et and no effect on $H_1$.

Anal. calculated for $C_{14}H_{18}O_3$+0.06 $H_2O$: C 71.44, H 7.76, O 20.80; found: C 71.26, H 7.78, O 20.63.

1α-Benzyloxy-3α-carbethoxy-cyclobutane 29 cis:

Fraction 2; MW=234.296; I.R. (film): 2986, 2943, 2865, 1731, 1604, 1496, 1454; $^1$H (CDCl$_3$ at 400 MHz): d in PPM: 7.35 (s: Ph); 4.38 (s: $CH_2$, Bzl); 4.08 (q: $CH_2$, Et); 3.86 (quint: $H_1$); 2.60 (m: $H_3$); 2.40 (m: $H_{2b}$+$H_{4b}$); 2.20 (m: $H_{2a}$+$H_{4a}$); 1.32 (t: $CH_3$, Et); $^{13}$C (CDCl$_3$ at 100 MHz): d in PPM: 174.38: CO; 138.02: $C_{r\,Ph}$; 128.32: $C_{o\,Ph}$; 127.67: $C_{m\,Ph}$; 127.60: $C_{p\,Ph}$; 69.82: $C_1$; 68.28: $CH_2$, Bzl; 60.29: $CH_2$, Et; 33.69: $C_2$+$C_4$; 29.04: $C_3$; 13.88: $CH_3$, Et; $^1$H (CDCl$_3$ at 400 MHz) NOE experiments: irradiation on $H_{2b}$: positive NOE on $H_1$ and $H_3$; irradiation on $H_{2a}$: no effect on $H_3$ and $H_1$.

Anal. calculated for $C_{14}H_{18}O_3$, 0.11 $H_2O$: C 71.17, H 7.77, O 21.06; found: C 71.06, H 7.65, O 20.93.

EXAMPLE 23

1α-Benzyloxy-3α-carbethoxy-cyclobutane 29 cis and 1α-benzyloxy-3β-carbethoxy-cyclobutane 29 trans A solution of 4 (11.56 g, 37.76 mmoles), water (1.30 ml, 75.52 mmoles) and sodium chloride (2.21 g, 37.76 mmoles) in dimethylsulfoxide (19 ml) was heated at 210° C. for 48 hours (TLC control: tertiobutylmethylether/hexane=2/8). Three spots were visible on TLC: spot 1: Rf=0.28, 29 trans, spot 2: Rf=0.22, 29 cis, spot 3: Rf=0.18, diester 4. Brine (150 ml) was added and the solution extracted 7 times with diethylether (7×100 ml), which was dried over magnesium sulfate and evaporated to dryness. The mixture was separated by flash chromatography (eluent: tertiobutylmethylether/hexane=2/8 to 8/2). The fraction containing both isomers was chromatographed a second time with the same solvent to give fraction 1: Rf=0.28, compound 29 trans, 3.34 g, 37.9%; fraction 2: Rf=0.22, compound 29 cis, 4.43 g, 50.1%.

EXAMPLE 24

1α-Benzyloxy-3α-hydroxymethyl-cyclobutane 30 cis and 1α-benzyloxy-3β-hydroxymethyl-cyclobutane 30 trans Lithium aluminum hydride (1.39 g, 36.36 mmoles) was stirred under argon in dimethoxyethane (50 ml). The 1:1 mixture of the acids 27 cis and 27 trans (5.19 g, 24.21 mmoles) in dimethoxyethane (10 ml) was added dropwise without cooling. The suspension was mechanically stirred at 85° C. for 60 hours (TLC control: tertiobutylmethylether/hexane=9/1, only 1 spot was visible). After cooling, water (100 ml) was slowly added until the suspension turned from gray to white. This suspension was evaporated to dryness, a mixture of tetrahydrofuran and ethyl acetate 9/1 (100 ml) was added and the suspension filtered over Hyflo. The precipitate was washed 3 times with the same solvent mixture (3×50 ml) and the obtained solution was evaporated to dryness. The 1:1 mixture of the isomers was purified by flash chromatography (eluent: tertiobutylmethylether/hexane=1/1 to tertiobutyl-methylether) to afford 30 cis and 30 trans: 4.60 g, 98.8%; MW=192.258; $^1$H (CDCl$_3$ at 200 MHz): d in PPM: 7.36 (s: Ph); 4.32 (s: $CH_2$, Bzl); 4.30 (s: $CH_2$, Bzl); 4.15 (quint: $H_1$); 3.85 (quint: $H_1$); 3.60 (d: $CH_2OH$); 2.33 (m: $H_{2b}$+$H_{4b}$); 2.08 (m: $H_{2a}$+$H_{4a}$); 1.90 (m: $H_3$); $^{13}$C (CDCl$_3$ at 50 MHz): d in PPM: 138.79: $C_{r\,Ph}$; 138.74: $C_{r\,Ph}$; 128.93: $C_{o\,Ph}$; 128.46: $C_{m\,Ph}$; 128.41: $C_{p\,Ph}$; 128.18: $C_{p\,Ph}$; 72.22: $C_1$; 69.85: $C_1$; 70.37: $CH_2$, Bzl; 67.36: $CH_2OH$; 66.85: $CH_2OH$; 32.25: $C_2$; 32.00: $C_4$; 30.01: $C_3$; 28.52: $C_3$.

Anal. calculated for $C_{12}H_{16}O_2$: C 74.97, H 8.39, O 16.64; found: C 75.00, H 8.40, O 16.69.

EXAMPLE 25

1α-Benzyloxy-3α-hydroxymethyl-cyclobutane
30 cis:

Lithium aluminum hydride (607 mg, 16.00 mmoles) was stirred under argon in dimethoxyethane (50 ml). The ester 29 cis (5.13 g, 21.90 mmoles) was added neat dropwise without cooling. The suspension was mechanically stirred at 85° C. for 60 hours (TLC control: tertiobutylmethylether/hexane= 9/1). After cooling, water (100 ml) was slowly added until the suspension turned from gray to white. This suspension was evaporated to dryness, a mixture of tetrahydrofuran and ethyl acetate 9/1 (100 ml) was added and the obtained suspension filtered over Hyflo. The precipitate was washed 3 times with the same solvent mixture (3×50 ml) and the solution was evaporated to dryness. The compound was purified by flash chromatography (eluent: tertiobutylmethylether/hexane=1/1 to tertiobutylmethylether) to afford 30 cis: 3.87 g, 91.9%; MW=192.258; I.R. (film): 3398, 2974, 2991, 2933, 2861, 1951, 1878, 1812; $^1$H (CDCl$_3$ at 200 MHz): d in PPM: 7.33 (s: Ph); 4.30 (s: CH$_2$, Bzl); 3.86 (quint: H$_1$); 3.60 (d: CH$_2$OH); 2.33 (m: H$_{2b}$+H$_{4b}$); 2.08 (m: H$_{2a}$+H$_{4a}$); 1.90 (m: H$_3$); $^{13}$C (CDCl$_3$ at 50 MHz): d in PPM: 138.72: C$_{r\ Ph}$; 128.93: C$_{o\ Ph}$; 128.42: C$_{m\ Ph}$; 128.14: C$_{p\ Ph}$; 69.85: C$_1$; 70.37: CH$_2$, Bzl; 66.85: CH$_2$OH; 32.25: C$_2$; 32.00: C$_4$; 28.52: C$_3$.

Anal. calculated for C$_{12}$H$_{16}$O$_2$: C 74.97, H 8.39, O 16.64; found: C 75.00, H 8.40, O 16.69.

EXAMPLE 26

1α-Benzyloxy-3β-hydroxymethyl-cyclobutane
30 trans:

Analogous to the procedure for 30 cis, 29 trans (5.0 g, 21.34 mmoles) afforded 30 trans: 3.70 g, 90.2%; /MW= 192.258; I.R. (film): 3415, 3031, 2970, 2934, 2863, 1954, 1877, 1812; $^1$H (CDCl$_3$ at 200 MHz): d in PPM (J: Hz): 7.35 (s: Ph); 4.37 (s: CH$_2$, Bzl); 4.12 (quint: J: 6.5, H$_1$); 3.59 (d: J:7.0, CH$_2$OH); 2.35 (m: H$_3$); 2.11 (m: H$_2$+H$_4$); $^{13}$C (CDCl$_3$ at 50 MHz): d in PPM: 138.78: C$_{r\ Ph}$; 128.90: C$_{o\ Ph}$; 128.36: C$_{m\ Ph}$; 128.12: C$_{p\ Ph}$; 72.15: C$_1$; 70.34: CH$_2$, Bzl; 67.05: CH$_2$OH; 31.99: C$_2$+C$_4$; 29.96: C$_3$.

Anal. calculated for C$_{12}$H$_{16}$O$_2$: C 74.97, H 8.39, O 16.64; found: C 75.00, H 8.40, O 16.69.

EXAMPLE 27

1α-Benzyloxy-3α-tertiobutyldiphenylsilyloxymethyl-cyclobutane
31 cis:

Tertiobutyldiphenylchlorosilane (16.39 ml, 63.00 mmoles) was added neat at 0° C. under argon to a solution of 30 cis (10.09 g, 52.49 mmoles) and imidazole (7.15 g, 105.0 mmoles) in dimethylformamide (250 ml). The reaction mixture was stirred at room temperature for 20 hours (TLC control: tertiobutylmethylether/hexane=5/95). Two spots were visible on TLC: spot 1: 31 cis and spot 2: tertiobutyldiphenylsilylhydroxyde. Water (250 ml) was added and the solution extracted 3 times with ethyl acetate (3×300 ml). The combined organic phases were washed with water (150 ml) and brine (150 ml), dried over magnesium sulfate and evaporated to dryness. Flash chromatography (eluent: tertiobutylmethylether/hexane=1/99 to 5/95) afforded 31 cis (18.50 g, 81.2%) as a colourless oil; MW=430.665; I.R. (film): 3070, 3049, 2931, 2892, 2857, 1959, 1890, 1824, 1722, 1589, 1568; $^1$H (CDCl$_3$ at 200 MHz): d in PPM (J: Hz): 7.68 (m: 4 H$_{ar}$); 7.38 (m: 11 H$_{ar}$); 4.42 (s: CH$_2$, Bzl); 3.95 (quint: J: 6.0, H$_1$); 3.67 (d: J: 6.0, CH$_2$OSi); 2.33 (q: H$_{2a}$+H$_{4a}$); 2.10 (m: H$_3$); 1.87 (t: H$_{2b}$+H$_{4b}$); 1.10 (s: CH$_3$, tBu); $^{13}$C (CDCl$_3$ at 50 MHz): d in PPM: 139.04: C$_{r\ Ph}$; 136.18: C$_{o\ PhSi}$; 134.54: C$_{r\ PhSi}$; 130.10: C$_{p\ PhSi}$; 128.89: C$_{o\ Ph}$; 128.40: C$_{m\ Ph}$; 128.17: C$_{m\ PhSi}$; 128.07: C$_{p\ Ph}$; 70.19: CH$_2$, Bzl; 69.87: C$_1$; 67.94: CH$_2$OSi; 33.16: C$_2$+C$_4$; 28.53: C$_3$; 27.21: CH$_3$, tBu; 19.64: C, tBu; U.V. (methanol, 0.5×10$^{-4}$ mole/l): 1 max in nm (e max): 259 (840); 265 (920).

Anal. calculated for C$_{28}$H$_{34}$O$_2$Si: C 78.09, H 7.96, Si 6.52, O 7.43; found: C 78.02, H 8.18, Si 6.67.

EXAMPLE 28

1α-Benzyloxy-3β-tertiobutyldiphenylsilyloxymethylcyclobutane
31 trans:

Tertiobutyldiphenylchlorosilane (3.24 ml, 12.48 mmoles) was added neat at 0° C. under argon to a solution of 30 trans (2 g, 10.40 mmoles) and imidazole (1.42 g, 20.80 mmoles) in dimethylformamide (80 ml). The reaction mixture was stirred at room temperature for 64 hours (TLC control: tertiobutylmethylether/hexane=5/95). Two spots were visible on TLC: spot 1: 31 trans and spot 2: tertiobutyldiphenylsilylhydroxyde. Ethyl acetate (200 ml) and water (50 ml) were added and the aqueous phase extracted twice with ethyl acetate (2×200 ml). The combined organic phases were washed twice with brine (2×50 ml), dried over magnesium sulfate and evaporated to dryness. Flash chromatography (eluent: tertiobutylmethylether/hexane=1/99 to 5/95) afforded 31 trans (4.40 g, 98.2%) as a colourless oil; MW=430.665; I.R. (film): 3071, 3050, 3032, 2932, 2892, 2857, 1958, 1889, 1821, 1721, 1589; $^1$H (CDCl$_3$ at 200 MHz): d in PPM (J: Hz): 7.68 (m: 4 H$_{ar}$); 7.50→7.30 (m: 11 H$_{ar}$); 4.38 (s: CH$_2$, Bzl); 4.17 (quint: J: 6.0; H$_1$); 3.67 (d: J: 6.0, CH$_2$OSi); 2.42 (m: H$_3$); 2.15 (m: H$_2$+H$_4$); 1.05 (s: CH$_3$, tBu); $^{13}$C (CDCl$_3$ at 50 MHz): d in PPM: 138.50: C$_{r\ Ph}$; 136.18: C$_{o\ PhSi}$; 133.04: C$_{PhSi}$; 130.13: C$_{p\ Phs}$; 128.90: C$_{o\ Ph}$; 128.39: C$_{m\ Ph}$; 128.17: C$_{m\ PhSi}$; 128.07: C$_{p\ Ph}$; 72.08: C$_1$; 70.30: CH$_2$, Bzl; 67.43: CH$_2$OSi; 32.11: C$_2$+C$_4$; 30.06: C$_3$; 27.18: CH$_3$, tBu; 19.58: C, tBu; U.V. (methanol, 0.5×10$^{-4}$ mole/l): 1 max in nm (e max): 253 (800); 259 (960); 264 (760); 270 (640).

Anal. calculated for C$_{28}$H$_{34}$O$_2$Si: C 78.09, H 7.96, Si 6.52, O 7.43; found: C 77.80, H 7.95, Si 6.48.

EXAMPLE 29

1α-Hydroxy-3α-tertiobutyldiphenylsilyloxymethyl-cyclobutane 32 cis:

Degussa palladium (500 mg) in dimethoxyethane (250 ml) was first placed under a hydrogen atmosphere. 31 cis (10 g, 23.27 mmoles) was then added neat. The reaction mixture was shaken vigorously at room temperature under a hydrogen pressure of 1 atmosphere until 1 equivalent of hydrogen (209 ml) was absorbed (approximately 8 hours). After filtration of the catalyst over Hyflo, the solution was evaporated to dryness to afford 32 cis as a colourless syrup (7.80 g, 99.2%); MW=340.54; (tertiobutylmethylether/hexane=2/ 8), Rf=0.11; I.R. (film): 3342, 3135, 3071, 3050, 2929, 2893, 2856, 1959, 1888, 1824, 1776, 1741; $^1$H (CDCl$_3$ at 200 MHz): d in PPM (J: Hz): 7.70 (dd: 4 H$_{ar}$); 7.40 (s: C$_{p\ PhSi}$); 7.30 (dd: 4 H$_{ar}$); 4.27 (quint: J: 7.0, H$_1$); 3.67 (d: J: 7.0, CH$_2$OSi); 2.30 (m: ABX H$_2$+H$_{4a}$); 2.20 (m: H$_3$); 1.95 (m:

ABX $H_{2b}+H_{4b}$); 1.10 (s: $CH_3$, tBu); U.V. (methanol, 0.5× $10^{-4}$ mole/l): l max in nm (e max): 259 (600); 264 (640); 270 (440).

Anal. calculated for $C_{21}H_{28}O_2Si$: C 74.07, H 8.29, Si 8.25, O 9.39; found: C 74.29, H 8.12, Si 8.33.

EXAMPLE 30

1α-Hydroxy-3β-tertiobutyldiphenylsilyloxymethyl-cyclobutane 32 trans:

Analogous to the procedure for 32 cis, 31 trans (10 g, 23.27 mmoles) afforded 32 trans as a colourless syrup (7.95 g, 99.7%); MW=340.54; (tertiobutylmethylether/hexane=2/8), Rf=0.11; I.R. (film): 3070, 3050, 2960, 2920, 2850, 1960, 1890, 1820, 1770, 1740; $^1H$ ($CDCl_3$ at 200 MHz): d in PPM (J: Hz): 7.70 (dd: 4 $H_{ar}$) 7.45 (s: $C_{p\ PhSi}$); 7.40 (dd: 4 $H_{ar}$); 4.47 (quint: J: 7.0, $H_1$); 3.67 (d: J: 7.0, $CH_2OSi$); 2.44 (m: $H_3$); 2.25 (m: ABX $H_{2a}+H_{4a}$); 2.05 (m: ABX $H_{2b}+H_{4b}$); 1.10 (s: $CH_3$tBu); $^{13}C$ ($CDCl_3$ at 50 MHz): d in PPM: 136.16: $C_{o\ PhSi}$; 134.32: $C_{r\ PhSi}$; 130.18: $C_{p\ PhSi}$; 128.16: $C_{m\ PhSi}$; 67.31: $CH_2OSi$; 66.72: $C_1$; 35.26: $C_2+C_4$; 29.36: $C_3$; 27.15: $CH_3$, tBu; 19.58: C, tBu; U.V. (methanol, $0.5×10^{-4}$ mole/l): l max in nm (e max): 259 (760); 264 (800); 270 (560).

Anal. calculated for $C_{21}H_{28}O_2Si$: C 74.07, H 8.29, Si 8.25, O 9.39; found: C 74.06, H 8.21, Si 7.99.

EXAMPLE 31

1α-p-Bromo-benzenesulfonyloxy-3α-tertiobutyldiphenylsilyloxymethyl-cyclobutane 33 cis:

p-Bromo-benzenesulfonylchloride (3.02 g, 11.82 mmoles) was added neat at room temperature under argon to a solution of 32 cis (3.35 g, 9.85 mmoles) and triethylamine (9.60 ml, 68.96 mmoles) in dichloromethane (50 ml). The reaction mixture was stirred at room temperature for 15 hours (TLC control: tertiobutylmethylether/hexane=2/8: Rf=0.40). On TLC no more alcohol was visible. Brine (50 ml) was added and the reaction mixture extracted 3 times with ethyl acetate (3×200 ml). The combined organic fractions were washed with brine (50 ml), dried over sodium sulfate and evaporated to dryness. Flash chromatography (eluent: tertiobutylmethylether/hexane=5/95 to 1/9) afforded 33 cis: 4.20 g, 76.2%; MW=559.598; (tertiobutylmethylether/hexane=2/8), Rf=0.40; MP=83.5–84.5° C. after crystallization from diethylether; I.R. (film): 3071, 2931, 2893, 2857, 1576, 1471; $^1H$ ($CDCl_3$ at 200 MHz): d in PPM (J: Hz): 7.80→7.60 (m: 8 $H_{ar}$); 7.45→7.32 (m: 6 $H_{ar}$); 4.70 (quint: J: 7.0, $H_1$); 3.52 (d: J: 7.0, $CH_2OSi$); 2.30→1.95 (m: $H_2+H_3+H_4$); 1.05 (s : $CH_3$, tBu); $^{13}C$ ($CDCl_3$ at 50 MHz): d in PPM:136.50: $C_{r\ Brs}$; 136.10: $C_{o\ PhSi}$; 134.06: $C_{r\ PhSi}$; 133.08: $C_{m\ Brs}$; 130.24: $C_{p\ PhSi}$; 129.81: $C_{o\ Brs}$; 129.20: $C_{p\ Brs}$; 128.22: $C_{m\ PhSi}$; 72.39: $C_1$; 65.85: $CH_2OSi$; 32.85: $C_2+C_4$; 28.81: $C_3$; 27.13: $CH_3$, tBu; 19.59: C, tBu; U.V. (methanol, $0.5×10^{-4}$ mole/l): l max in nm (e max): 221 (23400); 256 (1200); 263 (1300).

Anal. calculated for $C_{27}H_{31}BrO_4SSi$: C 57.95, H 5.58, Br 14.28, S 5.73, Si 5.02; found: C 57.73, H 5.63, Br 14.11, S 5.67, Si 4.85.

EXAMPLE 32

1α-p-Bromo-benzenesulfonyloxy-3β-tertiobutyldiphenylsilyloxymethyl-cyclobutane 33 trans:

p-Bromo-benzenesulfonylchloride (2.08 g, 8.14 mmoles) was added neat at room temperature under argon to a solution of 32 trans (2.31 g, 6.78 mmoles) and triethylamine (6.61 ml, 47.48 mmoles) in dichloromethane (50 ml). The reaction mixture was stirred at room temperature for 36 hours (TLC control: tertiobutylmethylether/hexane=2/8: Rf: 0.40). Another two portions of p-bromo-benzenesulfonylchloride (2×200 mg, 2×0.81 mmoles) were added. On TLC no more alcohol was visible. Brine (30 ml) was added and the reaction mixture extracted 3 times with ethyl acetate (3×200 ml). The combined organic fractions were washed with brine (50 ml), dried over sodium sulfate and evaporated to dryness to afford 33 trans: 3.04 g, 80.1%; MW: 559.598; (tertiobutylmethylether/hexane:=2/8), Rf=0.40; MP=80–81° C. after crystallization from diethylether; I.R. (film): 3070, 2940, 2880, 2860, 1580, 1470; $^1H$ ($CDCl_3$ at 200 MHz): d in PPM (J: Hz): 7.80→7.60 (m: 8 $H_{ar}$); 7.45→7.32 (m: 6 $H_{ar}$); 4.98 (quint: J: 7.0, $H_1$); 3.58 (d: J: 7.0, $CH_2OSi$); 2.30 (m: $H_2+H_3+H_4$); 1.05 (s: $CH_3$, tBu); $^{13}C$ ($CDCl_3$ at 50 MHz): d in PPM: 136.51: $C_{r\ Brs}$; 136.13: $C_{O\ PhSi}$; 134.02: $C_{r\ PhSi}$; 133.08: $C_{m\ Brs}$; 131.12: $C_{o\ Brs}$; 130.51: $C_{p\ PhSi}$; 129.20: $C_{p\ Brs}$; 128.20: $C_{m\ PhSi}$; 75.46: $C_1$; 65.92: $CH_2OSi$; 32.90: $C_2+C_4$; 30.15: $C_3$; 27.16: $CH_3$, tBu; 19.56: C, tBu; U.V. (methanol, $0.5×10^{-4}$ mole/l): l max in nm (e max): 220 (23060); 233 (16500); 259 (1300); 259 (1300); 265 (1400).

Anal. calculated for $C_{27}H_{31}BrO_4SSi$: C 57.95, H 5.58, Br 14.28, S 5.73, Si 5.02; found: C 57.96, H 5.69, Br 14.00, S 5.61, Si 4.85.

EXAMPLE 33

1α-Adenyl (9)-3α-tertiobutyldiphenylsilyloxymethyl-cyclobutane 34 cis and 1α-adenyl (7)-3α-tertiobutyldiphenylsilyloxymethyl-cyclobutane 35 cis:

A mixture of 33 trans (2.78 g, 4.96 mmoles), adenine (19.84 g, 26.82 mmoles) and diazabicycloundecene (3.02 ml, 2.96 mmoles) in dimethylsulfoxide (28 ml) were stirred under argon at 80° C. for 15 hours (TLC control: tertiobutylmethylether/methanol=8/2; detection: 1) chlorine 2) potassium iodide). Three spots were visible on TLC: spot 1: Rf=0.95, unreacted 33 trans; spot 2: Rf=0.88, compound 34 cis; spot 3: Rf=0.57, compound 35 cis. Brine (200 ml) and water (800 ml) were added and the solution was extracted 7 times with ethyl acetate (4×75 ml). The combined organic fractions were washed with brine (50 ml), dried over sodium sulfate and purified by flash chromatography (tertiobutylmethylether/methanol=98/2 to 1/1) to afford fraction 1: compound 33 trans, 735 mg, 26.0%; fraction 2: compound 34 cis, 1.06 g, 46.8%; fraction 3: compound 35 cis, 190 mg, 8.4%.

1α-Adenyl (9)-3α-tertiobutyldiphenylsilyloxymethyl-cyclobutane 34 cis:

Fraction 2; MW=457.65; MP=181–182° C.; I.R. (KBr): 3324, 3160, 2929, 2855, 1662, 1601, 1571; $^1H$ ($CDCl_3$ at 200 MHz): d in PPM: 8.35 (s: $H_{2ad}$); 7.88 (s: Head); 7.67 (m: 4 $H_{ar}$); 7.37 (m: 6 $H_{ar}$); 5.98 (s: $NH_2$) 4.92 (quint: $H_1$); 3.22 (s: $CH_2OSi$); 2.65→2.35 (m: $H_2+H_3+H_4$); 1.10 (s: $CH_3$, tBu); $^{13}C$ ($CDCl_3$ at 50 MHz): d in PPM: 156.11: $C_{6ad}$; 153.46: $C_{2ad}$; 152.05: $C_{4ad}$; 139.16: $C_{8ad}$; 136.16: $C_{o\ PhSi}$; 134.07: $C_{r\ PhSi}$; 130.21: $C_{p\ PhSi}$; 128 27: $C_{m\ PhSi}$; 118.43: $C_{5ad}$; 65.85: $CH_2OS$; 45.13: $C_1$; 32.61 $C_2+C_4$; 30.82: $C_3$; 27.21: $CH_3$, tBu; 19.62: C, tBu; U.V. (water, $0.5×10^{-4}$ mole/l): l max in nm (e max): 204 (34780); 258 (12920).

Anal. calculated for $C_{26}H_{31}N_5OSi$: C 68.24, H 6.83, N 15.30, Si 6.14; found: C 68.09, H 6.84, N 15.43, Si 6.18.

1α-Adenyl (7)-3α-tertiobutyldiphenylsilyloxymethyl-cyclobutane 35 cis:

Fraction 3, $C_{26}H_{31}N_5OSi$, MW=457.65, I.R. (KBr) 3071, 2931, 2857, 1922, 1895, 1870, 1844, 1800, 1773, 1751, 1654, 1619, 1578; $^1H$ (CDCl$_3$ at 200 MHz): d in PPM: 8.10 (s : $H_{2ad}$); 8.02 (s: $H_{8ad}$); 7.65 (m: 4 $H_{ar}$); 7.37 (m: 6 $H_{ar}$); 5.12 (quint: $H_1$); 3.71 (s: CH$_2$OSi); 2.70 (m: $H_{2a}+H_{4a}$); 2.45 (m: $H_{2b}+H_3+H_{4b}$); 1.05 (s: CH$_3$, tBu); U.V. water, $0.5\times10^{-4}$ mole/l): l max in nm (e max): 214 (29800); 277 (16280).

EXAMPLE 34

1α-Adenyl (9)-3β-tertiobutyldiphenylsilyloxy methyl-cyclobutane 34 trans and 1α-adenyl (7)-3β-tertiobutyldiphenylsilyloxymethyl-cyclobutane 35 trans:

A mixture of 33 cis (3.81 g, 6.81 mmoles), adenine (3.68 g, 27.22 mmoles) and diazabicycloundecene (4.05 ml, 4.14 mmoles) in dimethylsulfoxide (38 ml) were stirred under argon at 80° C. for 35 hours (TLC control: tertiobutylmethylether/methanol=8/2; detection: 1) chlorine 2) potassium iodide). Two spots were visible on TLC: spot 1: Rf=0.95, unreacted 33 cis; spot 2: Rf =0.88, compound 34 trans; spot 3: Rf=0.57, compound 35 trans. Brine (200 ml), water (800 ml) were added and the solution was extracted 7 times with ethyl acetate (4×75 ml). The collected organic fractions were washed with brine (50 ml), dried over sodium sulfate and purified by flash chromatography (tertiobutylmethylether/methanol=98/2 to 1/1) to afford fraction 1: compound 33 cis, 1.29 g, 33.9%; fraction 2: compound 34 trans, 1.46 g, 46.9%; fraction 3: compound 35 trans, 401 mg, 12.9

1α-Adenyl (9)-3β-tertiobutyldiphenylsilyloxymethyl-cyclobutane 34 trans:

Fraction 2; MW=457.65; MP=129.5–130.5° C.; I.R. (KBr): 3138, 2929, 2857, 1660, 1651, 1645, 1650, 1600, 1574; $^1H$ (CDCl$_3$ at 200 MHz): d in PPM: 8.35 (s: $H_{2ad}$); 7.90 (s: $H_{8ad}$); 7.67 (m: 4 $H_{ar}$); 7.37 (m: 6 $H_{ar}$); 6.78 (s: NH$_2$); 5.10 (quint: $H_1$); 3.77 (s: CH$_2$OSi); 2.60→2.45 (m: $H_2+H_3+H_4$); 1.10 (s: CH$_3$, tBu); $^{13}C$ (CDCl$_3$ at 50 MHz): d in PPM: 156.98: $C_{6ad}$; 153.34: $C_{2ad}$; 150.53: $C_{4ad}$; 139.28 $C_{8ad}$; 136.16: $C_{o\,PhSi}$; 134.14: $C_{r\,PhSi}$; 130.30: $C_{p\,PhSi}$; 128 29: $C_{m\,PhSi}$; 120.43: $C_{5ad}$; 66.54: CH$_2$OSi; 47.98: $C_1$; 31.82: $C_2+C_4$; 31.48: $C_3$; 27.23: CH$_3$, tBu; 19.60: C, tBu; U.V. (water, $0.5\times10^{-4}$ mole/l): l max in nm (e max): 205 (40000); 258 (13940).

Anal. calculated for $C_{26}H_{31}N_5OSi$: C 68.24, H 6.82, N 15.30, Si 6.14; found: C 68.45, H 7.07, N 14.95, Si 5.93.

1α-Adenyl (9)-3β-tertiobutyldiphenylsilyloxymethyl-cyclobutane 35 trans:

Fraction 3, $C_{26}H_{31}N_5OSi$, MW=457.65; I.R. (KBr) 3322, 2933, 2894, 2857, 2244, 2218, 1658, 1618, 1549; $^1H$ (CDCl$_3$ at 200 MHz): d in PPM: 8.10 (s: $H_{2ad}$); 8.02 (s: $H_{8ad}$); 7.65 (m: 4 $H_{ar}$); 7.37 (m: 6 $H_{ar}$); 5.22 (quint: $H_1$); 3.81 (s: CH$_2$OSi); 2.87 (m: $H_{2a}+H_{4a}$); 2.60 (m: $H_{2b}+H_3+H_{4b}$); 1.05 (s: CH$_3$, tBu); U.V. (water, $0.5\times10^{-4}$ mole/l): l max in nm (e max): 214 (29800); 265 (9500).

EXAMPLE 35

1α-Adenyl (9)-3α-hydroxymethyl-cyclobutane 36 cis:

A solution of 34 cis (500 mg, 1.09 mmole) and aqueous hydrofluoric acid—urea (3 ml, 9 mmoles) in tetrahydrofuran (10 ml) was stirred for 15 hours at room temperature (TLC control: ethyl acetate/methanol=2/8; Rf=0.12). The reaction mixture was neutralized with sodium bicarbonate and evaporated to dryness. Purification by flash chromatography (ethyl acetate/methanol=9/1) afforded a mixture of 36 cis and sodium fluoride. Flash chromatography on hydrophobic silica gel first with water gave sodium fluoride and then with methanol gave 36 cis: 60 mg as a glassy solid; $^1H$ (CD$_3$OD at 200 MHz): d in PPM: 8.22 (s: $H_{2ad}$); 8.18 (s: $H_{9ad}$); 4.95 (quint: $H_1$); 3.62 (s: CH$_2$OH); 2.55 (m: $H_{2a}+H_{4a}$); 2.40 (m: $H_{2b}+H_3+H_{4b}$); $^{13}C$ (CD$_3$OD at 50 MHz): d in PPM: 157.20: $C_{6ad}$; 153.92: $C_{2ad}$; 149.10: $C_{4ad}$; 141.22: $C_{8ad}$; 111.60: $C_{5ad}$; 66.05: CH$_2$OH; 46.73: $C_1$; 35.57: $C_2+C_4$; 31.84: $C_3$; U.V. (ethanol, $0.5\times10^{-4}$ mole/l): l max in nm (e max): 206 (16580); 262 (11160); $C_{10}H_{13}N_2O_3$; MW=219.246; FAB-MS: M+Na=242; M+H$^+$=220; M–CH$_3$OH=188; Ad+H$^+$=136.

EXAMPLE 36

1α-Adenyl (9)-3β-hydroxymethyl-cyclobutane 36 trans:

Analogous to the procedure for 36 cis, 34 trans (500 mg, 1.09 mmole) afforded 36 trans, 60 mg, as a glassy solid; $^1H$ (CD$_3$OD at 200 MHz): d in PPM: 8.25 (s: $H_{2ad}$); 8.16 (s: $H_{8ad}$); 5.15 (quint: $H_1$); 3.62 (s: CH$_2$OH); 2.60 (m: $H_{2a}+H_{4a}$); 2.45 (m: $H_{2b}+H_3+H_{4b}$); $^{13}C$ (CD$_3$OD at 50 MHz): d in PPM: 157.3 $C_{6ad}$; 153.90: $C_{2ad}$; 149.20: $C_{4ad}$; 141.44: $C_{8ad}$; 112.40: $C_{5ad}$; 66.21: CH$_2$OH; 48.5: $C_1$; 35.75: $C_2+C_4$; 31.80: $C_3$; U.V. (ethanol, $0.5\times10^{-4}$ mole/l): l max in nm (e max): 206 (16250); 262 (11050); $C_{10}H_{13}N_2O_3$; MW=219.246; FAB-MS: M+Na=242; M+H$^+$=220; M–CH$_3$OH=188; Ad+H$^+$=136.

EXAMPLE 37

Synthesis of Oligonucleotide Surrogates—Phosphotriester Method

1. Phosphorylation:

A typical activated phosphoryl compound was prepared as follows: 1α-(N-Benzoyl-adenyl)-3α-hydroxymethyl-3β-methoxytrityloxymethyl-cyclobutane 22 (0.25 mmole, 156.4 mg) was co-evaporated with pyridine to remove traces of water and phosphorylated with 2-chlorophenyl-di-(1-benzotriazolyl)-phosphate (1.00 ml, 0.25 M) in THF at room temperature for 30 min (activated nucleotide) as per: Van Boom, J. H., Van der Marel, G. A., Van Boeckel, C. A. A., Wille, G. and Hoyng, C. Chemical and Enzymatic Synthesis of Gene Fragments, A Laboratory Manual, edited by H. G. Gassen and Anne Lang, Verlag Chemie Weinheim/Deerfield Beach, Fla./Basel 1982. This intermediate, which can be kept in solution for several hours, was further processed in-situ.

In a like manner the corresponding guanine, cytosine, uracil and thymine compounds are prepared.

2. Assembling of the nucleotides on a solid-phase:

11.5 mg of 3' (MeOTr-adenosine(Bz))-succinylamidomethyl-polystyrene (1% DVB crosslinked) (functionalization=2.24 mmoles), see Ito, H., Ike, Y., Ikuta, S. and Itakura, K. (1982) Nucleic Acids Research, 10:1755, was subjected to the following washing (3 ml/min) and reaction procedures: (dichloromethane-isopropanol=85:15 ) (3 min), MeOTr-cleavage: 1 M ZnBr$_2$, 0.02 M 1,2,4-triazole in dichloromethane-isopropanol (85:15) (1.5–2 min), see Rink, H., Liersch, M., Sieber, P. and Meyer, F. (1984) Nucleic Acids Research, 12:6369, dichloromethane-isopropanol (85:15) (3 min), 0.5 M triethylammonium-acetate in DMF (3 min), acetonitrile (<0.005% water) (3 min), nitrogen flow 50° C. (10 min).

Coupling: 64 ml activated carbanucleotide (16 mmol) and 6.4 ml N-methylimidazole (80 mMol), 12–15 min, 50° C., no flow, acetonitrile (4 min).

This solid-phase process was repeated seven times. Yield per coupling step: 80–87%, i.e., 0.6 μmol or 46 OD units calculated yield.

The oligomer was cleaved from the carrier and the protecting groups removed by sequentially reacting the resin with 1 M tetramethylguanidinium 2-nitrobenzaldoximate in 200 ml 95% pyridine during 7 h at 60° C. and 0.8 ml 33% aqueous ammonia for 24 h at 60° C. The reaction mixture was extracted 3 times with diethylether (2 ml each) and the aqueous phase was applied to a Biogel P4 (50–100 mesh) column (3×26 cm) and the product eluted with water. Fractions were checked for correct size of the oligomer and homogeneity with polyacrylamide- or capillary-electrophoresis. No further purification was usually needed, however in view of the coupling yields with 22, additional fractionation was performed on a Mono Q HR5/5 anion-exchanger. The applied gradient was: A=10 mM NaOH, 0.05 M NaCl; B=10 mM NaOH, 2 M NaCl; 0% B→40% B linear in 45 min. Fractions homogeneous in electrophoresis were checked with electrospray ionization mass spectrometry for the presence of the expected oligomer and were appropriately pooled and desalted on a Biogel P4 column. 10 ODs (optical units 259 nm) of octamer 24 and 7 ODs of the heptamer were isolated.

EXAMPLE 38

Synthesis of Oligonucleotide Surrogates—Phosphoramidate Method

1. Phosphoramidation:

A typical activated phosphoramidate is prepared as follows: 1α-(N-Benzoyladenyl)-3β-hydroxymethyl-3α-methoxytrityloxymethyl-cyclobutane 23 (1.89 mmol) is dissolved in anhydrous dichloromethane (13 ml) under an argon atmosphere, diisopropylethylamime (0.82 ml, 4.66 mmol) is added, and the reaction mixture cooled to ice temperature. Chloro(diisopropylamino)-β-cyanoethoxyphosphine (0.88 ml, 4.03 mmol) is added to the reaction mixture and the reaction mixture is then allowed to warm to 20° C. and stirred for 3 hours. Ethylacetate (80 ml) and triethylamine (1 ml) are added and the solution is washed with brine solution three times (3×25 ml). The organic phase is separated and dried over magnesium sulfate. After filtration of the solids the solvent is evaporated in vacuo at 20° C. to an oil that is then purified by column chromatography using silica and a solvent such as hexane-ethyl acetate-triethylamine (50:49:1) as eluent. The fractions are then evaporated in vacuo and the residue further evaporated with anhydrous pryidine (20 ml) in vacuo (1 torr) at 26° C. in the presence of sodium hydroxide for 24 hr. This will yield 1α-(N-Benzoyladenyl)-3β-(9-cyanoethyldiisopropylaminophosphityl) oxymethyl-3α-methoxytrityloxymethyl-cyclobutane.

In a like manner the corresponding guanine, cytosine, uridine and thymine compounds are prepared.

2. Assembly of Oligonucleotide Surrogates Using Standard Phosphoramidate Oligonucleotide Surrogate Synthesis Phosphoramidate oligonucleotide surrogates syntheses are performed on an Applied Biosystems 380 B or 394 DNA synthesizer following standard phosphoramidate protocols and cycles. The oligonucleotide subunits are as described above and all other reagents are as supplied by the manufacture. In those steps wherein phosphoramidite subunits of the oligonucleotide surrogates of the invention are used, a longer coupling time (10–15 min) is employed. The oligonucleotide surrogates are normally synthesized in either a 10 μmol scale or a 3×1 μmol scale in the "Trityl-On" mode. Standard deprotection conditions (30% NH$_4$OH, 55° C., 16 hr) are employed. HPLC is performed on a Waters 600E instrument equipped with a model 991 detector. For analytical chromatography, the following reverse phase HPLC conditions are employed: Hamilton PRP-1 column (15×2.5 cm); solvent A: 50 mm TEAA, pH 7.0; solvent B: 45 mm TEAA with 80% CH$_3$CN; flow rate: 1.5 ml/min; gradient: 5% B for the first 5 minutes, linear 1% increase in B every minute thereafter. For preparative purposes, the following reverse phase HPLC conditions are employed: Waters Delta Pak Waters Delta-Pak C$_4$ 15 μm, 300A, 25×100 mm column equipped with a guard column of the same material; column flow rate: 5 ml/min; gradient: 5% B for the first 10 minutes, linear 1% increase for every minute thereafter. Following HPLC purification, the oligonucleotide surrogates are detritylated and further purified by size exclusion using a Sephadex G-25 column.

3. Assembly of Phosphorothioate Oligonucleotide Surrogates Using Standard Phosphoramidate Oligonucleotide Surrogate Synthesis In a manner as per Example 38-2, the oligonucleotide surrogate is treated with the Beaucage reagent, i.e. 3H-1,2-benzodithioate-3-one 1,1-dioxide, see Radhakrishnan, P. I., Egan, W., Regan, J. B. and Beaucage, S. L., (1990), *J. Am. Chem. Soc.*, 112:1253 for conversion of the phosphordiester linkages to phosphorothioate linkages.

EVALUATION

PROCEDURE 1—Hybridization Analysis.

As with an oligonucleotide, the relative ability of an oligonucleotide surrogate of the invention to bind to complementary nucleic acids can be compared by determining the melting temperature of a particular hybridization complex. The melting temperature ($T_m$), a characteristic physical property of double-stranded RNA or DNA, denotes the temperature in degrees centigrade at which 50% helical versus coil (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$. Consequently, absolute fidelity of base pairing is necessary to have optimal binding of an antisense oligonucleotide to its targeted RNA or DNA.

A. Evaluation of the Thermodynamics of Hybridization of Oligonucleotide Surrogates.

The ability of the oligonucleotide surrogates of the invention to hybridize to their complementary RNA or DNA sequences was determined by thermal melting analysis. The RNA complements used were poly-rA and poly-rU. The DNA complements used were poly-da and (dT)$_8$. Additionally oligonucleotide surrogates of the invention were hybridized against one another and the $T_m$s determined. The oligonucleotide surrogates were added to either the RNA or DNA complement at stoichiometric concentrations and the absorbance (260 nm) hyperchromicity upon duplex to random coil transition was monitored using a Gilford Response II spectrophotometer. Such measurements are performed in a buffer of 10 mM Na-phosphate, pH 7.4, 0.1 mM EDTA, and 1M NaCl. The data was analyzed by a graphic representation of 1/$T_m$, vs ln[Ct], where [Ct] is the total oligonucleotide concentration.

The results of the thermodynamic analysis is shown in Tables 1 and 2. In both tables both measured $T_m$s and the percent hyperchromicity are shown. Table 1 shows results against other "normal" nucleic acid strands (that is ribofuranosyl or deoxy-ribofuranosyl based nucleic acid strands) and Table 2 shows results against complementary cyclobutane strands-that is against one another.

For these tables pseudo βA refers to an 8 mer oligonucleotide surrogate of the invention formed from eight cyclobutane units wherein the adenine base is cis to the methoxytrityloxymethyl moiety, i.e. compound 22, 1-α(N-benzoyl-adenyl)-3α-hydroxymethyl-3β-methoxytrityloxymethyl-cyclobutane. Pseudo αA refers to the corresponding 8 mer having the respective substituents of the cyclobutane ring trans to each other. In a like manner pseudo βT and pseudo αT reference the corresponding 8 mer cis and trans thymine base oligonucleotide surrogates.

TABLE 1

Melting Temperature, $T_m$, and % Hyperchromicity Of The Hybridization Complex Of The Oligonucleotide Surrogate and Complementary Nucleic Acid Strands
$T_m$ and
(% Hyperchromicity)

| Oligomer | Complementary Strand | | | |
|---|---|---|---|---|
|  | poly-rA | poly-dA | poly-rU | (dT)$_8$ |
| pseudo βA |  |  | 9° (16%) | 28° (25%) |
| pseudo αA |  |  | 55° (42%) | 22° (27%) |
| pseudo βT | 11° (23%) | 27° (24%) |  |  |
| pseudo αT |  | 10° (10%) |  |  |

TABLE 2

Melting Temperature, $T_m$, and % Hyperchromicity Of The Hybridization Complex Of The Oligonucleotide Surrogates With One Another
$T_m$ and
(% Hyperchromicity)

| Oligomer | Complementary Strand | |
|---|---|---|
|  | pseudo βT | pseudo αT |
| pseudo βA | 20° (28%) | 9° (14%) |
| pseudo αA | 18° (28%) | 12° (16%) |

B. Fidelity of Hybridization of Oligonucleotide Surrogates

The ability of the antisense oligonucleotide surrogates of the invention to hybridize with absolute specificity to a targeted mRNA can be shown by Northern blot analysis of purified target mRNA in the presence of total cellular RNA. Target mRNA is synthesized from a vector containing the cDNA for the target mRNA located downstream from a T7 RNA polymerase promoter. Synthesized mRNA is electrophoresed in an agarose gel and transferred to a suitable support membrane (i.e. nitrocellulose). The support membrane is blocked and probed using [_P]-labeled oligonucleotide surrogates. The stringency is determined by replicate blots and washing in either elevated temperatures or decreased ionic strength of the wash buffer. Autoradiography is performed to assess the presence of heteroduplex formation and the autoradiogram quantitated by laser densitometry (LKB Pharmacia, Inc.). The specificity of hybrid formation is determined by isolation of total cellular RNA by standard techniques and its analysis by agarose electrophoresis, membrane transfer and probing with the labelled oligonucleotide surrogates. Stringency is predetermined for an unmodified antisense oligonucleotide and the conditions used such that only the specifically targeted mRNA is capable of forming a heteroduplex with the oligonucleotide surrogate.

PROCEDURE 2—Nuclease Resistance

A. Evaluation of the Resistance of Oligonucleotide Surrogates to Serum and Cytoplasmic Nucleases.

Oligonucleotide surrogates of the invention can be assessed for their resistance to serum nucleases by incubation of the oligonucleotide surrogate in media containing various concentrations of fetal calf serum or adult human serum. Labeled oligonucleotide surrogates are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide surrogate, it is possible to determine the effect on nuclease degradation by the particular modification. For the cytoplasmic nucleases, an HL 60 cell line can be used. A post-mitochondrial supernatant is prepared by differential centrifugation and the labelled oligonucleotide surrogates are incubated in this supernatant for various times. Following the incubation, the oligonucleotide surrogates are assessed for degradation as outlined above for serum nucleolytic degradation. Autoradiography results are quantitated for comparison of the unmodified and the oligonucleotide surrogates of the invention. It is expected that the oligonucleotide surrogates will be completely resistant to serum and cytoplasmic nucleases.

B. Evaluation of the Resistance of Oligonucleotide Surrogates to Specific Endo- and Exo-Nucleases.

Evaluation of the resistance of natural oligonucleotides and oligonucleotide surrogates of the invention to specific nucleases (ie, endonucleases, 3', 5'-exo-, and 5', 3'-exonucleases) can be done to determine the exact effect of the modified linkage on degradation. The oligonucleotide surrogates are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the modified linkage are determined for specific nucleases and compared with the results obtained from the serum and cytoplasmic systems. As with the serum and cytoplasmic nucleases, it is expected that the oligonucleotide surrogates of the invention will be completely resistant to endo- and exonucleases.

PROCEDURE 3—5-Lipoxygenase Analysis, Therapeutics and Assays

A. Therapeutics

For therapeutic use, an animal suspected of having a disease characterized by excessive or abnormal supply of 5-lipoxygenase is treated by administering oligonucleotide surrogates of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide surrogates of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100% to about 500 ng per 10 mg of total RNA in a buffer consisting, for example, of 50 mm phosphate, pH ranging from about 4–10 at a temperature from about 30° to about 50° C. The cleaved 5-lipoxygenase RNA can be analyzed by agarose gel electrophoresis and hybridization with radiolabeled DNA probes or by other standard methods.

C. Diagnostics

The oligonucleotide surrogates of this invention will also be useful in diagnostic applications, particularly for the determination of the expression of specific mRNA species in various tissues or the expression of abnormal or mutant RNA species. In this example, the oligonucleotide surrogates target a hypothetical abnormal mRNA by being designed complementary to the abnormal sequence, but would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte-like cell or neutrophil-like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of antisense oligonucleotides surrogates which interfere with 5-lipoxygenase synthesis in these cells.

A second test system for antisense oligonucleotides surrogates makes use of the fact that 5-lipoxygenase is a "suicide" enzyme in that it inactivates itself upon reacting with substrate. Treatment of differentiated HL-60 or other cells expressing 5 lipoxygenase, with 10 $\mu$M A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Oligonucleotide surrogates directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

The most direct effect which oligonucleotide surrogates can exert on intact cells and which can be easily quantitated is specific inhibition of 5-lipoxygenase protein synthesis. To perform this technique, cells can be labelled with $^{35}$S-methionine (50 $\mu$Ci/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 $\mu$M, 10 $\mu$M, and 30 $\mu$M of effective oligonucleotide surrogates for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 $\mu$M $^{14}$C-arachidonic acid, 2 mM ATP, 50 $\mu$M free calcium, 100 $\mu$g/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak $C_{18}$ column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective oligonucleotide surrogates at 1 $\mu$M, 10 $\mu$M, and 30 $\mu$M would be as follows. Control cells oxidize 200 pmol arachidonic acid/5 min/$10^6$ cells. Cells treated with 1 $\mu$M, 10 $\mu$M, and 30 $\mu$M of an effective oligonucleotide surrogates would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 40° C. The wells are blocked for 90 min with 5% goat serum diluted in 20 mM Tris•HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 µL in the microtiter wells for 90 min. The antibodies are prepared by immunizing rabbits with purified human recombinant 5-lipoxygenase. The wells are washed with TBS containing 0.05% tween 20 (TBST), then incubated with 100 µL of a 1:1000 dilution of peroxidase conjugated goat anti-rabbit IgG (Cappel Laboratories, Malvern n, Pa.) for 60 min at 25° C. The wells are washed with TBST and the amount of peroxidase labelled second antibody determined by development with tetramethylbenzidine.

Predicted results from such an assay using a 30 mer oligonucleotide analog at 1 µM, 10 µM, and 30 µM would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells ($2 \times 10^5$ cells/mL) will be treated with increasing concentrations of oligonucleotide surrogates for 48–72 hours in the presence of 1.3% DMSO. The cells are washed and resuspended at a concentration of $2 \times 10^6$ cell/mL in Dulbecco's phosphate buffered saline containing 1% delipidated bovine serum albumin. Cells are stimulated with 10 µM calcium ionophore A23187 for 15 min and the quantity of LTB4 produced from $5 \times 10^5$ cell determined by radioimmunoassay as described by the manufacturer.

Using this assay the following results would likely be obtained with a 15-mer oligonucleotide surrogate of the sequence (GCAAGGTCACTGAAG) (SEQ ID NO: 1) directed to the 5-LO mRNA. Cells will be treated for 72 hours with either 1 µM, 10 µM or 30 µM oligonucleotide surrogate in the presence of 1.3% DMSO. The quantity of LTB$_4$ produced from $5 \times 10^5$ cells would be expected to be about 75 pg, 50 pg, and 35 pg, respectively with untreated differentiated cells producing 75 pg LTB$_4$.

E. In Vivo Assay

Inhibition of the production of 5-lipoxygenase in the mouse can be demonstrated in accordance with the following protocol. Topical application of arachidonic acid results in the rapid production of leukotriene B$_4$, leukotriene C$_4$ and prostaglandin E$_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene B$_4$ produced in biopsy specimens is performed as a direct measurement of 5-lipoxygenase activity in the tissue. Oligonucleotide surrogates will be applied topically to both ears 12 to 24 hours prior to administration of arachidonic acid to allow optimal activity of the compounds. Both ears are pretreated for 24 hours with either 0.1 µmol, 0.3 µmol, or 1.0 µmol of the oligonucleotide analog prior to challenge with arachidonic acid. Values are expressed as the mean for three animals per concentration. Inhibition of polymorphonuclear cell infiltration for 0.1 µmol, 0.3 µmol, and 1 µmol is expected to be about 10%, 75% and 92% of control activity, respectively. Inhibition of edema is expected to be about 3%, 58% and 90%, respectively while inhibition of leukotriene B$_4$ production would be expected to be about 15%, 79% and 99%, respectively.

PROCEDURE 4—ANTIVIRAL ACTIVITY

Certain of the heterocyclic base substituted cyclobutane compound of the invention were tested as to their antiviral activity. Both 1-adenyl-3,3-bis-hydroxymethyl-cyclobutane and 1-thyminyl-3,3-bis-hydroxymethyl-cyclobutane were tested against HSV-1 in human macrophages. Both of these compounds were tested up to 600 µg/ml without toxicity. In these tests 1-thyminyl-3,3-bis-hydroxymethyl-cyclobutane exhibited a MED$_{50}$ of 40–65 µµg/ml and 1-adenyl-3,3-bis-hydroxymethyl-cyclobutane exhibited a MED$_{50}$ of 200 µg/ml. Both of these compounds showed no activity in a cellular HIV assay.

---

We claim:

1. A composition comprising:
   a pharmaceutically effective amount of a compound formed from a plurality of cyclobutyl moieties covalently joined by linking moieties, wherein each of said cyclobutyl moieties includes an attached purine or an attached pyrimidine heterocyclic base; and
   a pharmaceutically acceptable diluent or carrier.

2. The composition of claim 1 wherein said purine or pyrimidine heterocyclic base is a naturally-occurring or synthetic purin-9-yl, pyrimidin-1-yl or pyrimidin-3-yl heterocyclic base.

3. The composition of claim 1 wherein:
   said heterocyclic base is attached to each respective cyclobutyl moiety at a C-1 position of said cyclobutyl moiety; and
   each of said linking moieties connects to two of the cyclobutyl moieties at a C-3 position of the cyclobutyl moieties.

4. The composition of claim 1 wherein each of said linking moieties comprises a 4 atom or a 5 atom chain that joins two of the cyclobutyl moieties.

5. The composition of claim 4 wherein each of said linking moieties is of the structure

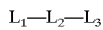

where:
   $L_1$ and $L_3$ are $CH_2$; and
   $L_2$ is phosphodiester, phosphorothioate, phosphoramidate, phosphotriester, $C_1$–$C_6$ alkyl phosphonate, phosphorodithioate, phosphonate, carbamate, sulfonate, $C_1$–$C_6$-dialkylsilyl or formacetal.

6. The composition of claim 4 wherein each of said linking moieties is of the structure:

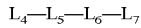

where:
(a) $L_4$ and $L_7$ are $CH_2$; and $L_5$ and $L_6$, independently, are $CR_1R_2$, $C=CR_1R_2$, $C=NR_3$, $C=O$, $C=S$, $O$, $S$, $SO$, $SO_2$, $NR_3$ or $SiR_4R_5$; or (b) $L_4$ and $L_7$ are $CH_2$; and $L_5$ and $L_6$, together, are $CR_1=CR_2$, $C\equiv C$, part of a $C_6$ aromatic ring, part of a $C_3$–$C_6$ carbocyclic ring or part of a 3, 4, 5 or 6 membered heterocyclic ring; or (c) $L_4$—$L_5$—$L_6$—$L_7$, together, are $CH=N$—$NH$—$CH_2$ or $CH_2$—$O$—$N=CH$;

where:
   $R_1$ and $R_2$, independently, are H, OH, SH, $NH_2$, $C_1$–$C_{10}$ alkyl, $C_1$–$C_{10}$ substituted alkyl, $C_1$–$C_{10}$ alkenyl, $C_7$–$C_{10}$ aralkyl, $C_1$–$C_6$ alkoxy, $C_1$–$C_6$ thioalkoxy, $C_1$–$C_6$ alkylamino, $C_7$–$C_{10}$ aralkylamino, $C_1$–$C_{10}$ substituted alkylamino, heterocycloalkyl, heterocycloalkylamino, aminoalkylamino, polyalkylamino, halo, formyl, keto, benzoxy, carboxamido, thiocarboxamido, ester, thioester, carboxamidino, carbamyl, ureido, guanidino, or an RNA cleaving group;
   $R_3$ is H, OH, $NH_2$, $C_1$–$C_6$ alkyl, substituted lower alkyl, alkoxy, lower alkenyl, aralkyl, alkylamino, aralkylamino, substituted alkyl amino, heterocycloalkyl, heterocycloalkylamino, aminoalkylamino, polyalkylamino, or a RNA cleaving group; and
   $R_4$ and $R_5$, independently, are $C_1$–$C_6$ alkyl or alkoxy.

7. The composition of claim 4 wherein each of said linking moieties is $CH=N$—$NH$—$CH_2$, $CH_2$—$NH$—$NH$—$CH_2$, $CH_2$—$O$—$NH$—$CH_2$ or $CH_2$—$O$—$N=CH$.

8. The composition of claim 4 wherein:
   said purine or pyrimidine heterocyclic base is adenine, guanine, cytosine, thymine, uracil 5-methylcytosine, hypoxanthine or 2-aminoadenine;
   said heterocyclic base is attached to each respective cyclobutyl moiety at a C-1 position of said cyclobutyl moiety; and
   each of said linking moieties connects to two of the cyclobutyl moieties at a C-3 position of the cyclobutyl moieties.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 15 bases
      (B) TYPE: nucleic acid
      (C) STRANDEDNESS: single
      (D) TOPOLOGY: linear (xi) SEQUENCE DESCRIPTION: SEQ ID NO:1:

GCAAGGTCAC TGAAG                      15